(12) United States Patent
Di Paolo et al.

(10) Patent No.: US 9,974,792 B2
(45) Date of Patent: *May 22, 2018

(54) METHODS FOR TREATING CANCERS

(71) Applicant: Gilead Sciences, Inc., Foster City, CA (US)

(72) Inventors: Julie Di Paolo, San Francisco, CA (US); Michael J. Hawkins, San Francisco, CA (US); Jing Hu, Foster City, CA (US); Feng Jin, Foster City, CA (US); Flordeliza Melchor-Khan, Palo Alto, CA (US); Anita Reddy, Foster City, CA (US)

(73) Assignee: Gilead Sciences, Inc., Foster City, CA (US)

( * ) Notice: Subject to any disclaimer, the term of this patent is extended or adjusted under 35 U.S.C. 154(b) by 0 days. days.

This patent is subject to a terminal disclaimer.

(21) Appl. No.: 15/603,663

(22) Filed: May 24, 2017

(65) Prior Publication Data
US 2017/0258804 A1    Sep. 14, 2017

Related U.S. Application Data

(63) Continuation of application No. 14/559,707, filed on Dec. 3, 2014, now Pat. No. 9,687,492.

(60) Provisional application No. 61/911,978, filed on Dec. 4, 2013.

(51) Int. Cl.
*A61K 31/5377* (2006.01)

(52) U.S. Cl.
CPC .................. *A61K 31/5377* (2013.01)

(58) Field of Classification Search
None
See application file for complete search history.

(56) References Cited

U.S. PATENT DOCUMENTS

| | | | |
|---|---|---|---|
| 5,593,997 | A | 1/1997 | Dow et al. |
| 5,658,857 | A | 8/1997 | Andree et al. |
| 5,783,576 | A | 7/1998 | Roos et al. |
| 5,846,514 | A | 12/1998 | Foster et al. |
| 6,334,997 | B1 | 1/2002 | Foster et al. |
| 6,919,340 | B2 | 7/2005 | Currie et al. |
| 6,919,341 | B2 | 7/2005 | Paruch et al. |
| 7,160,885 | B2 | 1/2007 | Currie et al. |
| 7,189,723 | B2 | 3/2007 | Mitchell et al. |
| 7,259,164 | B2 | 8/2007 | Mitchell et al. |
| 7,312,341 | B2 | 12/2007 | DeSimone et al. |
| 7,405,295 | B2 | 7/2008 | Currie et al. |
| 8,440,667 | B2 | 5/2013 | Mitchell et al. |
| 8,450,321 | B2 | 5/2013 | Mitchell et al. |
| 8,455,493 | B2 | 6/2013 | Mitchell et al. |
| 8,697,699 | B2 | 4/2014 | Mitchell et al. |
| 8,748,607 | B2 | 6/2014 | Mitchell et al. |
| 8,765,761 | B2 | 7/2014 | Mitchell et al. |
| 8,796,270 | B2 | 8/2014 | Mitchell |
| 8,962,835 | B2 | 2/2015 | Mitchell et al. |
| 9,120,811 | B2 | 9/2015 | Mitchell et al. |
| 9,212,191 | B2 | 12/2015 | Mitchell et al. |
| 9,290,505 | B2 | 3/2016 | Blomgren et al. |
| 9,376,441 | B2 | 6/2016 | Currie et al. |
| 9,382,256 | B2 | 7/2016 | Casteel et al. |
| 9,504,684 | B2 | 11/2016 | Blomgren et al. |
| 9,562,056 | B2 | 2/2017 | Blomgren et al. |

(Continued)

FOREIGN PATENT DOCUMENTS

| | | |
|---|---|---|
| CA | 2175837 A1 | 5/1995 |
| DE | 4337609 A1 | 5/1995 |

(Continued)

OTHER PUBLICATIONS

National Caancer institute cancer tyoes (2017).*
ClinicalTrials.gov/ct2/show/NCT01799889 Jul. 3, 2013.*
CancerConnect (Aug. 17, 2013).*
Al-Dabbagh, S. G. et al. (1984). "Species Differences in Oxidative Drug Metabolism: Some Basic Considerations." Archives of Toxicology. Supplement. Archive fur Toxikologie. Supplement, 7:219-231.
Bastin et al, (2000), Org. Proc. Res. Dev., vol. 4, No. 5, pp. 427-435.
Berge et al, J Pharm Sci 1977, vol. 66, Issue 1, pp. 1-19.
Bouloc et al., Bioorg Med Chem Ltrs vol. 20 Iss 20 (2010) pp. 5988-5993.
Bundgaard, H., (1985). *Design of Prodrugs*, Elsevier Science Publishers, B.V., The Netherlands, p. 1.

(Continued)

*Primary Examiner* — Shirley V Gembeh
(74) *Attorney, Agent, or Firm* — Sheppard Mullin Richter & Hampton LLP

(57) ABSTRACT

Disclosed are methods for treating a cancer in a subject (e.g., a human) in need thereof, comprising administering to the subject a therapeutically effective amount of a compound of formula I:

(I)

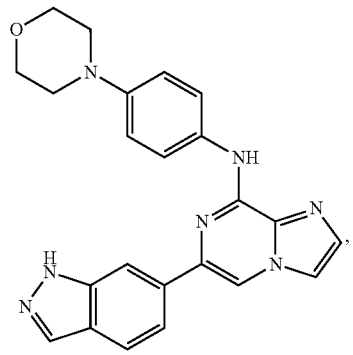

or a pharmaceutically acceptable salt thereof. The subject may be very high risk or high risk for the cancer. The subject who has the cancer may also be refractory to at least one chemotherapy treatment, or is in relapse after treatment with chemotherapy, or both. The cancer may be a hematologic malignancy, such as leukemia or lymphoma.

19 Claims, 9 Drawing Sheets

(56) References Cited

U.S. PATENT DOCUMENTS

| | | |
|---|---|---|
| 9,567,348 B2 | 2/2017 | Mitchell et al. |
| 9,657,023 B2 | 5/2017 | Elford et al. |
| 9,687,492 B2 | 6/2017 | Di Paolo et al. |
| 9,707,236 B2 | 7/2017 | Di Paolo et al. |
| 9,796,718 B2 | 10/2017 | Mitchell et al. |
| 2003/0212073 A1 | 11/2003 | Currie et al. |
| 2004/0063715 A1 | 4/2004 | Paruch et al. |
| 2004/0067951 A1 | 4/2004 | DeSimone et al. |
| 2004/0072835 A1 | 4/2004 | Paruch et al. |
| 2004/0102455 A1 | 5/2004 | Burns et al. |
| 2004/0220189 A1 | 11/2004 | Sun et al. |
| 2005/0009832 A1 | 1/2005 | Sun et al. |
| 2005/0054648 A1 | 3/2005 | Mitchell et al. |
| 2005/0054649 A1 | 3/2005 | Currie et al. |
| 2005/0085484 A1 | 4/2005 | Mitchell et al. |
| 2005/0090499 A1 | 4/2005 | Currie et al. |
| 2005/0101604 A1 | 5/2005 | Currie et al. |
| 2005/0288295 A1 | 12/2005 | Currie et al. |
| 2006/0069084 A1 | 3/2006 | Burns et al. |
| 2006/0084650 A1 | 4/2006 | Dong et al. |
| 2006/0183746 A1 | 8/2006 | Currie et al. |
| 2007/0117804 A1 | 5/2007 | Zhao et al. |
| 2009/0221612 A1 | 9/2009 | Mitchell et al. |
| 2010/0152159 A1 | 6/2010 | Mitchell et al. |
| 2010/0222323 A1 | 9/2010 | Mitchell et al. |
| 2012/0220582 A1 | 8/2012 | Mitchell et al. |
| 2013/0023499 A1 | 1/2013 | Mitchell et al. |
| 2013/0210802 A1 | 8/2013 | Blomgren et al. |
| 2013/0231330 A1 | 9/2013 | Mitchell et al. |
| 2013/0237520 A1 | 9/2013 | Mitchell et al. |
| 2013/0237521 A1 | 9/2013 | Mitchell et al. |
| 2013/0267496 A1 | 10/2013 | Mitchell et al. |
| 2013/0310363 A1 | 11/2013 | Mitchell et al. |
| 2013/0338142 A1 | 12/2013 | Blomgren et al. |
| 2014/0148430 A1 | 5/2014 | Blomgren et al. |
| 2014/0357627 A1 | 12/2014 | Mitchell et al. |
| 2015/0038488 A1 | 2/2015 | Currie et al. |
| 2015/0038504 A1 | 2/2015 | Casteel et al. |
| 2015/0038505 A1 | 2/2015 | Elford et al. |
| 2015/0150881 A1 | 6/2015 | Di Paolo et al. |
| 2015/0175616 A1 | 6/2015 | Blomgren et al. |
| 2016/0166580 A1 | 6/2016 | Casteel et al. |
| 2016/0168155 A1 | 6/2016 | Fung et al. |
| 2016/0220573 A1 | 8/2016 | Di Paolo et al. |
| 2016/0310490 A1 | 10/2016 | Blomgren et al. |
| 2016/0368918 A1 | 12/2016 | Blomgren et al. |
| 2016/0375019 A1 | 12/2016 | Di Paolo et al. |
| 2017/0020821 A1 | 1/2017 | Casteel et al. |
| 2017/0035755 A1 | 2/2017 | Blomgren et al. |
| 2017/0095490 A1 | 4/2017 | Blomgren et al. |
| 2017/0121350 A1 | 5/2017 | Blomgren et al. |
| 2017/0217967 A1 | 8/2017 | Elford et al. |

FOREIGN PATENT DOCUMENTS

| | | |
|---|---|---|
| EP | 480713 A1 | 4/1992 |
| JP | 2001-302667 A | 10/2001 |
| JP | 2004-528295 A | 9/2004 |
| JP | 2005-530739 A | 10/2005 |
| JP | 2008-519843 A | 6/2008 |
| JP | 2010-546786 A | 2/2009 |
| JP | 2011-511835 A | 4/2011 |
| NZ | 593460 A | 11/2013 |
| WO | WO-1988/04298 A1 | 6/1988 |
| WO | WO-1995/12594 A1 | 5/1995 |
| WO | WO-1996/04298 A1 | 2/1996 |
| WO | WO-1996/34866 A1 | 11/1996 |
| WO | WO-1999/28322 A1 | 6/1999 |
| WO | WO-01/27119 A2 | 4/2001 |
| WO | WO-2001/83485 A1 | 11/2001 |
| WO | WO-2002/10170 A1 | 2/2002 |
| WO | WO-2002/30428 A1 | 4/2002 |
| WO | WO-2002/060492 | 8/2002 |
| WO | WO-2002/066481 A1 | 8/2002 |
| WO | WO-2002/076985 A1 | 10/2002 |
| WO | WO-2003/070732 A1 | 8/2003 |
| WO | WO-2003/089434 A2 | 10/2003 |
| WO | WO-2003/089434 A3 | 10/2003 |
| WO | WO-2004/022562 A1 | 3/2004 |
| WO | WO-2004/026310 A1 | 4/2004 |
| WO | WO-2004/026867 A2 | 4/2004 |
| WO | WO-2004/026877 A1 | 4/2004 |
| WO | WO-2004/072080 A1 | 8/2004 |
| WO | WO-2004/072081 A1 | 8/2004 |
| WO | WO-2005/005429 A1 | 1/2005 |
| WO | WO-2005/014599 A1 | 2/2005 |
| WO | WO-2005/019220 A2 | 3/2005 |
| WO | WO-2005/047290 A2 | 5/2005 |
| WO | WO-2005/085252 A1 | 9/2005 |
| WO | WO-2006/044687 A2 | 4/2006 |
| WO | WO-2006/053121 A2 | 5/2006 |
| WO | WO-2008/025821 A1 | 3/2008 |
| WO | WO-2009/077334 A1 | 6/2009 |
| WO | WO-2009/102468 A1 | 8/2009 |
| WO | WO-2010/006947 A1 | 1/2010 |
| WO | WO-2010/027500 A1 | 3/2010 |
| WO | WO-2010/068257 A1 | 6/2010 |
| WO | WO-2010/068258 A1 | 6/2010 |
| WO | WO-2011/112995 A1 | 9/2011 |
| WO | WO-2013/049750 | 4/2013 |
| WO | WO-2014/028665 A1 | 2/2014 |
| WO | WO-2015/017466 | 2/2015 |

OTHER PUBLICATIONS

Dean, D.C. (2000). "Recent Advances in the Synthesis and Applications of Radiolabeled Compounds for Drug Discovery and Development," Curr. Pharm Des. 6(10): Preface, 1 page.

Ding, S. et al. (2002) "A Combinatorial Scaffold Approach Toward Kinase-Directed Heterocycle Libraries," J. Am Chem Soc., 124(8):1594-1596.

Elder, et al, (2010) J Pharm Sci, vol. 99, Issue 7, pp. 2948-2961.

European Communication dated Jun. 18, 2013, for EP Patent Application No. 11 709 600.8 filed on Mar. 11, 2011, 6 pages. (39.45).

European Communication dated Jun. 6, 2013, for EP Patent Application No. 09 832 228.2 filed on Jun. 21, 2011, 5 pages. (27.49).

European Communication dated Oct. 24, 2012, for European Patent Application No. 09710901.1, filed on Feb. 12, 2009, five pages. (38.43).

Evans, E.A. (1981). "Synthesis of Radiolabeled Compounds," J. Radioanal. Chem. 64(1-2):9-32.

Extended European Search Report dated Apr. 26, 2012, for EP 09 83 2229, filed on Jun. 21, 2011, 6 pages. (28.48).

Extended European Search Report dated Jul. 27, 2012, for EP 09 83 2228.2, filed on Jun. 21, 2011, 12 pages. (27.49).

Extended European Search Report dated Mar. 12, 2014, for EP 13005979.3, filed on Dec. 20, 2013, 5 pages. (27.64).

Final Office Action dated Jan. 27, 2012, for U.S. Appl. No. 12/632,151, filed Dec. 7, 2009, 15 pages. (28.00).

Final Office Action dated May 2, 2013 for U.S. Appl. No. 13/343,624, filed Jan. 4, 2012, 9 pages. (38.01).

Final Office Action dated May 25, 2012, for U.S. Appl. No. 12/632,140, filed Dec. 7, 2009, 9 pages. (27.00).

Final Office Action dated Oct. 30, 2012, for U.S. Appl. No. 12/632,140, filed Dec. 7, 2009, 9 pages. (27.00).

Final Office Action dated Sep. 15, 2011, for U.S. Appl. No. 12/632,140, filed Dec. 7, 2009, 15 pages. (27.00).

Final Office Action dated Sep. 5, 2012, for U.S. Appl. No. 12/632,151, filed Dec. 7, 2009, 11 pages. (28.00).

GenBank Accession No. AY050647.1, created on Oct. 7, 2001, located at <http://www.ncbi.nlm.nih.gov/nuccore/AY050647.1>, last visited on Dec. 28, 2011, 1 page.

Hackam, D.G. et al. (2006). "Translation of Research Evidence From Animals to Humans," JAMA 296(14):1731-1732.

International Preliminary Examination Report dated Aug. 5, 2004, for PCT Application No. PCT/US2003/12222, filed Apr. 21, 2003, 11 pages.

International Preliminary Examination Report dated Oct. 27, 2004, for PCT Application No. PCT/US2003/28329, filed on Sep. 9, 2003, 5 pages.

(56) References Cited

OTHER PUBLICATIONS

International Preliminary Report on Patentability dated Jan. 5, 2011, for PCT Application No. PCT/US2009/006445, filed on Dec. 7, 2009, 6 pages. (27.40).
International Preliminary Report on Patentability dated Oct. 29, 2010, for PCT Application No. PCT/US/2009/006446, filed on Dec. 7, 2009, 6 pages. (28.40).
International Preliminary Report on Patentability dated Aug. 17, 2010, for PCT Application No. PCT/US2009/000919, filed on Feb. 12, 2009, 8 pages. (38.40).
International Search Report and Written Opinion dated Oct. 13, 2014, for PCT Application No. PCT/US2014/048741, Filed Jul. 29, 2014.
International Search Report and Written Opinion dated Dec. 30, 2004, for PCT Application No. PCT/US2004/018227, filed on Jun. 4, 2004, 10 pages.
International Search Report and Written Opinion dated Dec. 8, 2004, for PCT Application No. PCT/US2004/021150, filed on Jun. 30, 2004, 10 pages.
International Search Report and Written Opinion dated Feb. 1, 2005 for PCT Application No. PCT/US2004/025884, filed on Aug. 11, 2004, 8 pages.
International Search Report and Written Opinion dated Jul. 7, 2004, for PCT Application No. PCT/US2004/003922, filed on Feb. 10, 2004, 12 pages.
International Search Report and Written Opinion dated Jul. 7, 2004, for PCT Application No. PCT/US2004/003923, filed on Feb. 10, 2004, 12 pages.
International Search Report and Written Opinion dated Jun. 23, 2005, for PCT Application No. PCT/US2004/037433, filed on Nov. 10, 2004, 15 pages.
International Search Report and Written Opinion dated Mar. 3, 2015, for PCT Application No. PCT/US2014/068423, Filed Dec. 3, 2014.
International Search Report and Written Opinion dated Oct. 8, 2014, for PCT Application No. PCT/US2014/048733, filed on Jul. 29, 2014.
International Search Report dated Apr. 26, 2011, for Application No. PCT/US2011/028194, filed on Mar. 11, 2011, 5 pages. (39.40).
International Search Report dated Feb. 12, 2010, for PCT Application No. PCT/US/2009/006446, filed on Dec. 7, 2009, 3 pages. (28.40).
International Search Report dated Feb. 12, 2010, for PCT Application No. PCT/US2009/006445, filed on Dec. 7, 2009, 3 pages. (27.40).
International Search Report dated Feb. 9, 2004, for PCT Application No. PCT/US2003/28329, filed on Sep. 9, 2003.
International Search Report dated May 12, 2009, for PCT Application No. PCT/US2009/000919, filed on Feb. 12, 2009, 5 pages. (38.40).
International Search Report dated May 3, 2015, for PCT Application No. PCT/US2014/071842, filed Dec. 22, 2014, 3 pgs.
International Search Report dated Oct. 22, 2003, for PCT Application No. PCT/US2003/12222, filed on Apr. 21, 2003.
Invitation to Pay Additional Fees with Partial International Search Report dated May 3, 2005, for PCT Application No. PCT/US2004/037433, filed on Nov. 10, 2004, 9 pages.
Japanese Decision of Patent dated Feb. 4, 2014, for Japanese Patent Application No. 2010-546786, filed on Aug. 1, 2010, 4 pages. (with English translation). ( 38.45 ).
Japanese Notice of Reasons for Rejection dated Feb. 4, 2014 for Japanese Patent Application No. 2011-539524, filed on Jun. 6, 2011, 10 pages. (with English translation). (27.53).
Japanese Notice of Reasons for Rejection dated Feb. 6, 2014, for Japanese Patent Application No. 2011-539525, filed on Jun. 6, 2011, 11 pages. (with English translation). (28.52).
Jeffrey,T.K. et al. (1998). "Phosphodiesterase III and V Inhibitors on Pulmonary Artery from Pulmonary Hypertensive Rats: Differences Between Early and established Pulmonary Hypertension", *J. Cardiovascular Pharmacology*, 32(2): 213-219.

Jordan, V.C. (Mar. 2003). "Tamoxifen: A Most Unlikely Pioneering Medicine" *Nature Reviews: Drug Discovery* 2:205-213.
Kabalka, G.W. et al. (1989). "The Synthesis of Radiolabeled Compounds via Organometallic Intermediates," *Tetrahedron* 45(21):6601-21.
Kuhnz, W. et al. (Jun. 11, 1998). "Predicting the Oral Bioavailability of 19-Nortestosterone Progestins In Vivo From Their Metabolic Stability in Human Liver Microsomal Preparation In Vitro," *The American Society for Pharmacology and Experimental Therapeutics* 26(11)1120-1127.
Lumma, Jr., W.C. et al. (1983) "Piperazinylimidazo [1,2-a]pyrazines with Selective affinity for in Vitro a-Adrenergic Receptor Subtypes," *J. Med. Chem.* 26(3):357-363.
Non-Final Office Action dated Apr. 13, 2011 for U.S. Appl. No. 12/370,103, filed Feb. 12, 2009, 11 pages. (38.00).
Non-Final Office Action dated Apr. 3, 2006, for U.S. Appl. No. 10/776,002, filed Feb. 10, 2004, 13 pages (33.30).
Non-Final Office Action dated Dec. 31, 2013, for U.S. Appl. No. 13/901,523, filed May 23, 2013, 22 pages. (27.02).
Non-Final Office Action dated Feb. 17, 2012 for U.S. Appl. No. 12/632,140, filed Dec. 7, 2009, 11 pages. (27.00).
Non-Final Office Action dated Jan. 25, 2013, for U.S. Appl. No. 13/343,624, filed Jan. 4, 2012, 18 pages. (38.01).
Non-Final Office Action dated Jan. 8, 2007, for U.S. Appl. No. 10/915,696, filed Aug. 11, 2004, 8 pages. (34.00).
Non-Final Office Action dated Jun. 29, 2011, for U.S. Appl. No. 12/632,151, filed Dec. 7, 2009, 17 pages. (28.00).
Non-Final Office Action dated May 10, 2011 for U.S. Appl. No. 12/632,140, filed Dec. 7, 2009, 18 pages. (27.00).
Non-Final Office Action dated May 17, 2012, for U.S. Appl. No. 12/632,151, filed Dec. 7, 2009, 15 pages. (28.00).
Non-Final Office Action dated May 24, 2006, for U.S. Appl. No. 10/776,631, filed Feb. 10, 2004, 10 pages. (33.00).
Non-Final Office Action dated Nov. 4, 2013, for U.S. Appl. No. 13/862,147, filed Apr. 12, 2013, 18 pages. (28.01).
Non-Final Office Action dated Oct. 11, 2012, for U.S. Appl. No. 13/441,441, filed Apr. 6, 2012, 8 pages. (27.20).
Non-Final Office Action dated Oct. 11, 2013, for U.S. Appl. No. 13/868,967, filed Apr. 23, 2013, 17 pages. (27.01).
Non-Final Office Action dated Oct. 16, 2013, for U.S. Appl. No. 13/868,971, filed Apr. 23, 2013, 16 pages. (27.10).
Non-Final Office Action dated Sep. 26, 2006, for U.S. Appl. No. 10/658,121, filed Sep. 9, 2003, 7 pages. (32.00).
Notice of Allowance dated Apr. 20, 2007, for U.S. Appl. No. 10/915,696, filed Aug. 11, 2004, 7 pages. (34.00).
Notice of Allowance dated Aug. 11, 2006, for U.S. Appl. No. 10/776,002, filed Feb. 10, 2004, 10 pages. (33.30).
Notice of Allowance dated Aug. 8, 2007, for U.S. Appl. No. 10/658,121, filed Sep. 9, 2003, 4 pages. (32.00).
Notice of Allowance dated Mar. 6, 2007, for U.S. Appl. No. 10/658,121, filed Sep. 9, 2003, 6 pages. (32.00).
Notice of Allowance dated Aug. 12, 2013, for U.S. Appl. No. 13/343,624, filed Jan. 4, 2012 , 9 pages (38.01).
Notice of Allowance dated Dec. 26, 2013, for U.S. Appl. No. 13/343,624, filed Jan. 4, 2012 , 10 pages . (38.01).
Notice of Allowance dated Feb. 12, 2014, for U.S. Appl. No. 13/862,147, filed Apr. 12, 2013, 9 pages. (28.01).
Notice of Allowance dated Feb. 5, 2014, for U.S. Appl. No. 13/868,967, filed Apr. 23, 2013, 8 pages. (27.01).
Notice of Allowance dated Jan. 14, 2013, for U.S. Appl. No. 12/632,151, filed Dec. 7, 2009, 8 pages (28.00).
Notice of Allowance dated Jan. 25, 2013, for U.S. Appl. No. 12/632,140, filed Dec. 7, 2009, 8 pages (27.00).
Notice of Allowance dated Jan. 28, 2013, for U.S. Appl. No. 13/441,441, filed Apr. 6, 2012 , 8 pages (27.20).
Notice of Allowance dated Jan. 30, 2014, for U.S. Appl. No. 13/868,971, filed Apr. 23, 2013, 8 pages. (27.10).
Notice of Allowance dated Sep. 7, 2006, for U.S. Appl. No. 10/776,631, filed Feb. 10, 2004, 7 pages. (33.00).
Office Action dated Dec. 15, 2014 for Japan Patent Application No. 2014-095907.
Office Action dated Jan. 15, 2015 for Chilean Patent Application No. 1360-11.

(56) References Cited

OTHER PUBLICATIONS

Office Action dated Jan. 30, 2015 for Vietnamese Patent Application No. 1-2011-01623.
Office Action dated Feb. 18, 2015 for Eurasian Patent Application No. 201400197.
Office Action dated Mar. 30, 2015 for European Patent Application No. 13 005 979.3.
Oravcova, J. et al. (1996). "Drug-Protein Binding Studies New Trends in Analytical and Experimental Methodology," *J Chromatogr B* 677:1-28.
Paulekuhn et al., J Med Chem 2007, 50, pp. 6665-6672.
Resolution dated Dec. 18, 2014 for Colombian Patent Application No. 14-049.611.
Restriction Requirement dated Dec. 8, 2010, for U.S Appl. No. 12/632,140, filed Dec. 7, 2009, 10 pages. (27.00).
Restriction Requirement dated Jan. 27, 2006, for U.S. Appl. No. 10/776,631, filed Feb. 10, 2004, 6 pages. (33.00).
Restriction Requirement dated Jan. 30, 2006, for U.S. Appl. No. 10/658,121, filed Sep. 9, 2003, 5 pages. (32.00).
Restriction Requirement dated Jan. 4, 2006, for U.S. Appl. No. 10/776,002, filed Feb. 10, 2004, 7 pages. (33.30).
Restriction Requirement dated May 18, 2006, for U.S. Appl. No. 10/658,121, filed Sep. 9, 2003, 5 pages. (32.00).
Restriction Requirement dated Oct. 13, 2006, for U.S. Appl. No. 10/915,696, filed Aug. 11, 2004, 5 pages. (34.00).
Restriction Requirement dated Oct. 20, 2004, for U.S. Appl. No. 10/419,682, filed Apr. 21, 2003, 9 pages.
Restriction Requirement dated Apr. 14, 2014, for U.S. Appl. No. 13/862,194, filed Apr. 12, 2013, 5 pages. (28.10).
Restriction Requirement dated Dec. 8, 2010, for U.S. Appl. No. 12/632,151, filed Dec. 7, 2009, 10 pages. (28.00).
Restriction Requirement dated Feb. 17, 2011, for U.S. Appl. No. 12/370,103, filed Feb. 12, 2009, 10 pages. (38.00).
Restriction Requirement dated Jan. 27, 2014, for U.S. Appl. No. 13/609,068, filed Nov. 26, 2012, 8 pages. (39.00).
Restriction Requirement dated Jul. 26, 2012, for U.S. Appl. No. 13/441,441, filed Apr. 6, 2012, 9 pages. (27.20).
Restriction Requirement dated Jul. 3, 2013, for U.S. Appl. No. 13/868,971, filed Apr. 23, 2013, 5 pages. (27.10).
Restriction Requirement dated Jun. 14, 2013, for U.S. Appl. No. 13/862,147, filed Apr. 12, 2013, 10 pages. (28.01).
Restriction Requirement dated Jun. 24, 2013, for U.S. Appl. No. 13/868,967, filed Apr. 23, 2013, 10 pages. (27.01).
Restriction Requirement dated Nov. 27, 2012, for U.S. Appl. No. 13/343,624, filed Jan. 4, 2012, 10 pages. (38.01).
Restriction Requirement dated Oct. 15, 2013, for U.S. Appl. No. 13/901,523, filed May 23, 2013, 5 pages. (27.02).
Restriction Requirement dated Sep. 8, 2014, for U.S. Appl. No. 14/274,618, filed May 9, 2014, 6 pages. (27.03).
Second Written Opinion dated Apr. 13, 2004, for PCT Application No. PCT/US2003/12222, filed Apr. 21, 2003, 7 pages.
Silverman, R.B. (1992), *The Organic Chemistry of Drug Design and Drug Action*, Academic Press, Inc. San Diego, CA, pp. 352-400.
Stenberg, K.A.E. et al., (2000). "KinMutBase, a Database of Human Disease-Causing Protein Kinase Mutations", *Nucleic Acids Research* 28(1):369-371.
Taylor, R. et al., (1984). "Hydrogen-Bond Geometry in Organic Crystals", *Acc. Chem Res.* 17:320-326.

Vitse, O. et al. (1999). "New Imidazo [1,2-α]pyrazine Derivatives with Bronchodilatory and Cyclic Nucleotide Phosphodiesterase Inhibitory Activities," *Bioorganic and Medicinal Chemistry* 7:1059-1065.
Written Opinion dated Apr. 26, 2011, for Application No. PCT/US2011/028194, filed on Mar. 11, 2011, 6 pages. (39.40).
Written Opinion dated Dec. 5, 2003, for PCT Application No. PCT/US2003/12222, filed Apr. 21, 2003, 6 pages.
Written Opinion dated Jul. 6, 2004, for PCT Application No. PCT/US2003/28329, filed on Sep. 9, 2003, 5 pages. (32.40).
Written Opinion dated Feb. 12, 2010, for PCT Application No. PCT/US/2009/006446, filed on Dec. 7, 2009, 4 pages. (28.40).
Written Opinion dated Feb. 12, 2010, for PCT Application No. PCT/US2009/006445, filed on Dec. 7, 2009, 4 pages. (27.40).
Written Opinion dated May 12, 2009, for PCT Application No. PCT/US2009/000919, filed on Feb. 12, 2009, 7 pages.(38.40).
Zaragoza, D.F. (2005). *Side Reactions in Organic Synthesis: A Guide to Successful Synthesis Design*, Weinheim;Wiley-VCH Verlag GmbH &Co. KGaA, Preface, 2 pages.
Burke, R. et al (2013) "A Potential Therapeutic Strategy for Chronic Lymphocytic Leukemia by Combining Idelalisib and GS-9973, a Novel Spleen Tyrosine Kinase (Syk) Inhibitor", www.impactjournals.com/oncotarget/, Oncotarget, Advance Publications 2013, 1-8.
Currie, K. et al. (2014) "Discovery of GS-9973, a Selective and Orally Efficacious Inhibitor of Spleen Tyrosine Kinase" Journal of Medicinal Chemistry, 57, 3856-3873.
International Preliminary Report on Patentability dated Jun. 16, 2016 for PCT/US2014/068423.
Davids et al., Targeting the B cell receptor pathway in chronic lymphocytic leukemia, Leukemia & Lymphoma, 53(12):2362-2370 (2012).
Examination Report for Australia Patent Application No. 2014360537 dated Sep. 20, 2016. (3 pages).
Examination Report for New Zealand Application No. 718825 dated Oct. 28, 2016. (4 pages).
Examiner's Report for Canadian Application No. 2,932,726 dated Apr, 27, 2017. (3 pages).
Final Official Action for Japanese Application No. 2016-556694 dated Jul. 3, 2017. (6 pages).
Further Examination Report for New Zealand Application No. 718825 dated May 23, 2017. (3 pages).
Further Examination Report for New Zealand Application No. 718825 dated Sep. 15, 2017. (2 pages).
Makino et al., "Survey of Actual Concomitant Treatments with Antineoplastic Agents", Journal of Japanese Society Hospital Pharmacists, 44(2):223-228 (2008).
Notice of Final Rejection for Korean Application No. 10-2016-7017388 dated Oct. 30, 2017. (5 pages).
Notice of Preliminary Rejection for Korean Application No. 10-2016-7017388 dated Apr. 11, 2017. (7 pages).
Office Action for Chinese Application No. 201480064630.3 dated Jul. 25, 2017. (16 pages).
Official Action for Eurasian Application No. 201690608 dated Jul. 27, 2016. (4 pages).
Official Action for Japanese Application No. 2016-556694 dated Feb. 20, 2017. (5 pages).
Wierda, W. G., "Current and Investigational Therapies for Patients with CLL", Hematology 2006, p. 285-294.

* cited by examiner

METHODS FOR TREATING CANCERS

CROSS REFERENCE TO RELATED APPLICATIONS

This application is a continuation of U.S. application Ser. No. 14/559,707, filed on Dec. 3, 2014, now U.S. Pat. No. 9,687,492, which claims benefit under 35 U.S.C. § 119(e) to U.S. Provisional Application No. 61/911,978, filed on Dec. 4, 2013, the entirety of which is incorporated herein by reference.

FIELD

The present disclosure relates generally to the field of therapeutics and medicinal chemistry, and more specifically to the use of certain Spleen Tyrosine Kinase (Syk) inhibitors in the treatment of cancer including, for example, leukemia and lymphoma.

BACKGROUND

A number of imidazopyrazine compounds are under investigation for inhibiting Spleen Tyrosine Kinase (Syk) activity. Syk is a non-receptor tyrosine kinase that plays critical roles in immunoreceptor- and integrin-mediated signaling in a variety of cell types, including B-cells, macrophages, monocytes, mast cells, eosinophils, basophils, neutrophils, dendritic cells, T-cells, natural killer cells, platelets, and osteoclasts.

Syk has been reported to play an important role in signaling through the B-cell receptor, known to be an important survival signal in B-cells. As such, inhibition of Syk activity may be useful for treating certain types of hematologic malignancies. Examples of such hematologic malignancies include cancer, such as B-cell lymphoma and leukemia. Additionally, the inhibition of Syk activity is believed to be useful for treating of other diseases and conditions, including inflammatory diseases (e.g., rheumatoid arthritis), allergic disorders and autoimmune diseases.

One such compound that has been found to inhibit Syk activity is represented by formula I:

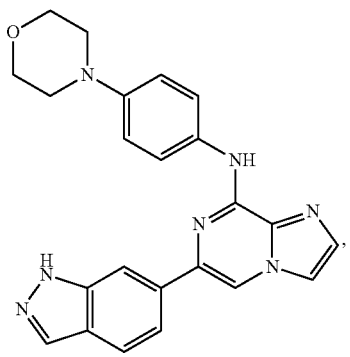
(I)

or a pharmaceutically acceptable salt thereof. This compound, also known as entospletinib, and its synthesis have been described in U.S. Pat. Nos. 8,450,321 and 8,455,493, which are hereby incorporated by reference in their entirety and specifically with respect to the method of making this compound. See e.g., U.S. Pat. No. 8,450,321, Examples 1 and 2.

It has been known that certain genomic aberrations are associated with resistance to treatment of B-cell lymphomas and leukemias, such as in the case of a 17p deletion, a TP53 mutation, a NOTCH1 mutation, a SF3B1 mutation, a 11q deletion, or any combination thereof, in patients experiencing chronic lymphocytic leukemia (CLL). Articles discussing the issue include 17p *Deletion is associated with resistance of B-cell chronic lymphocytic leukemia cells to in vitro fludarabine-induced apoptosis*, Turgut et al., Leukemia & Lymphoma, 2007, Vol. 48, No. 2: Pages 311-320; *Mutations of NOTCH1 are an independent predictor of survival in chronic lymphocytic leukemia*, Rossi et al., Blood, 2012, 119, pp. 521-529; *TP53 Mutation and Survival in Chronic Lymphocytic Leukemia*, Zenz et al., J. of Clin. Oncol., Vol. 28, No. 29, Oct. 10, 2010, pp. 4473-4479; *SF3B1 and Other Novel Cancer Genes in Chronic Lymphocytic Leukemia*, Wang et al., N Engl J Med 2011, 365, pp. 2497-2506; and *Mutation Status of the Residual ATM Allele Is an Important Determinant of the Cellular Response to Chemotherapy and Survival in Patients With Chronic Lymphocytic Leukemia Containing an 11q Deletion*, Austen et al., J. of Clin. Oncol., Vol. 25, No. 34, Dec. 1, 2007, pp. 5448-5457.

The Syk inhibitor fostamatinib was proposed as a therapy for B-cell malignancies on the basis of targeting Syk kinase (Sharman et al., *J Clin Oncol.* 2007; 25(suppl 18S)). Response rate to fostamatinib was reported as 54.5% based upon six subjects experiencing a partial lymph-node reduction of at least 50%. Unfortunately, fostamatinib treatment was associated with a relatively brief overall progression-free survival (PFS) of 18 weeks seen among participants treated in the phase 2 portion of the study, and PFS was 6.4 months for 11 subjects with CLL/SLL (Friedberg et al., *Blood.* 2010; 115(13):2578-2585). Further clinical development of fostamatinib has not been reported, and dose-limiting adverse events (AEs) possibly resulting from off-target activity of the agent highlight the need for more Syk-selective agents.

What is desired are methods for treating diseases responsive to the inhibition of Syk in subjects in need of such treatment, including in subjects who may be considered at risk for the disease, are refractory to standard treatments, and/or are in relapse after standard treatments, including those subjects with genomic aberrations that may be associated with resistance to treatments.

SUMMARY

Provided herein are methods for treating cancer in a subject in need thereof, comprising administering to the subject a therapeutically effective amount of a compound of formula I:

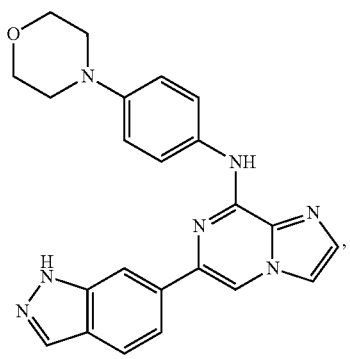
(I)

or a pharmaceutically acceptable salt thereof.

In some embodiments, the subject is a human who has a 17p deletion, a TP53 mutation, a NOTCH1 mutation, a SF3B1 mutation, a 11q deletion, or any combination thereof. In one embodiment, the subject is a human who has a 17p deletion, a TP53 mutation, or a combination thereof. In another embodiment, the subject is a human who has a NOTCH1 mutation, a SF3B1 mutation, a 11q deletion, or any combination thereof.

Provided herein are also methods for treating cancer in a subject in need thereof, comprising administering to the subject a therapeutically effective amount of a compound of formula I, or a pharmaceutically acceptable salt, wherein: the compound or the pharmaceutically acceptable salt thereof is the only anti-cancer therapy administered to the subject; and the subject is a human who is (i) refractory to at least one anti-cancer treatment, or (ii) in relapse after treatment with at least one anti-cancer therapy, or a combination thereof.

Provided herein are also methods for treating cancer in a subject in need thereof, comprising administering to the subject a therapeutically effective amount of a compound of formula I, or a pharmaceutically acceptable salt, wherein: the subject is a human who is not undergoing any other anti-cancer treatments; and the subject is (i) refractory to at least one anti-cancer treatment, or (ii) in relapse after treatment with at least one anti-cancer therapy, or a combination thereof.

In some embodiments, the subject is not undergoing any other anti-cancer treatments using one or more PI3K inhibitors. Such PI3K inhibitors may include, in certain embodiments, Compounds A (idelalisib), B (acalisib), and C, whose structures are provided below.

Compound A

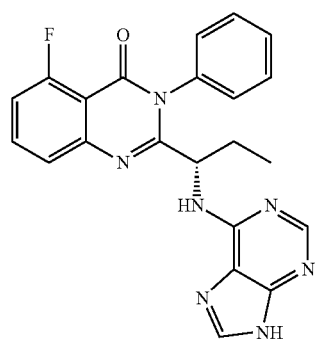

Compound B

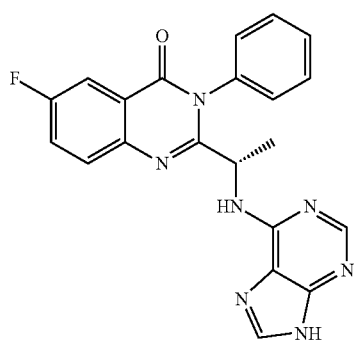

Compound C

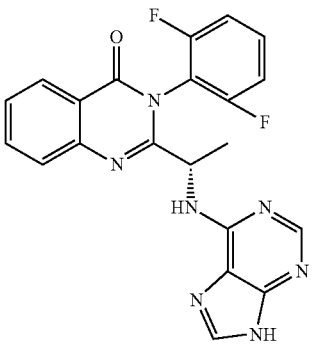

In some embodiments, the subject is refractory to at least one anti-cancer treatment. In other embodiments, the subject is in relapse after treatment with at least one anti-cancer treatment.

In some embodiments, about 500 mg to 1000 mg of the compound of formula I, or a pharmaceutically acceptable salt thereof, is administered to subject twice daily. In one embodiment, from about 600 mg to 1,000 mg of the compound of formula I, or a pharmaceutically acceptable salt thereof, is administered to subject twice daily. In another embodiment, from about 700 mg to 900 mg of the compound of formula I, or a pharmaceutically acceptable salt thereof, is administered to subject twice daily. In still another embodiment, about 800 mg of the compound of formula I, or a pharmaceutically acceptable salt thereof, is administered to subject twice daily.

In one variation, the subject is a human who has a 17p deletion, a TP53 mutation, or a combination thereof; and about 800 mg of the compound of formula I, or a pharmaceutically acceptable salt thereof, is administered to the subject twice daily.

In some embodiments, the cancer is a hematologic malignancy. In certain embodiments, the cancer is a leukemia. In one embodiment, the leukemia is chronic lymphocytic leukemia (CLL). In certain embodiments, the cancer is a lymphoma. In one embodiment, the lymphoma is non-Hodgkin's lymphoma (NHL). In one variation, the NHL is diffuse large B-cell lymphoma (DLBCL), mantle cell lymphoma (MCL), follicular lymphoma (FL), small lymphocytic lymphoma (SLL), lymphoplasmacytic lymphoma (LPL), and/or marginal zone lymphoma (MZL). Thus, it is understood that in one aspect the subject is a human who has a hematologic malignancy, such as leukemia or lymphoma.

In certain embodiments, the cancer is selected from the group consisting of acute lymphocytic leukemia (ALL), acute myeloid leukemia (AML), chronic lymphocytic leukemia (CLL), small lymphocytic lymphoma (SLL), myelodysplastic syndrome (MDS), myeloproliferative disease (MPD), chronic myeloid leukemia (CML), multiple myeloma (MM), non-Hodgkin's lymphoma (NHL), indolent non-Hodgkin's lymphoma (iNHL), refractory iNHL, mantle cell lymphoma (MCL), follicular lymphoma (FL), Waldestrom's macroglobulinemia (WM), T-cell lymphoma, B-cell lymphoma, diffuse large B-cell lymphoma (DLBCL), lymphoplasmacytic lymphoma (LPL), and marginal zone lymphoma (MZL).

DETAILED DESCRIPTION

Figure 1:
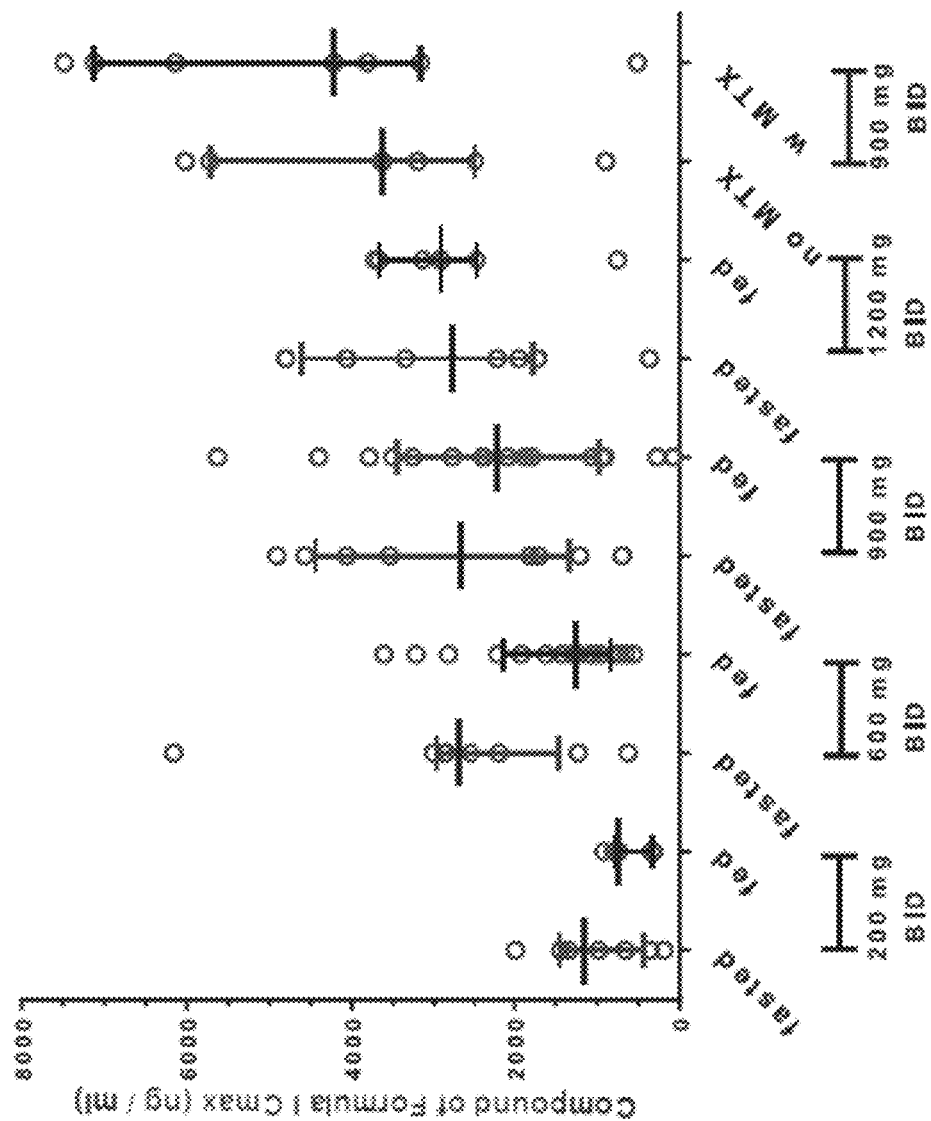
FIG. 1 is a graph depicting the maximum plasma levels of the compound of formula I, or a pharmaceutically acceptable salt thereof, at steady state in healthy human subjects.

The following description sets forth exemplary compositions and methods. It should be recognized, however, that such description is not intended as a limitation on the scope of the present disclosure but is instead provided as a description of exemplary embodiments.

Provided herein are methods for treating cancer in a certain population of subjects (e.g., humans) in need thereof, comprising administering to such subjects a therapeutically effective amount of a compound of formula I:

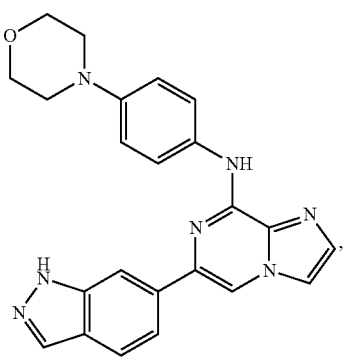

(I)

or a pharmaceutically acceptable salt.

The compound of formula I may also be referred to by its compound name: 6-(1H-indazol-6-yl)-N-(4-morpholinophenyl)imidazo[1,2-a]pyrazin-8-amine. The compound name provided is named using ChemBioDraw Ultra 12.0, and one skilled in the art understands that the compound structure may be named or identified using other commonly recognized nomenclature systems and symbols including CAS and IUPAC. One method for synthesizing the compound of formula I has been previously described in, for example, U.S. Pat. No. 8,450,321.

Any formula or structure given herein, including the compound of formula I and pharmaceutically acceptable salts thereof, is also intended to represent unlabeled forms as well as isotopically labeled forms of the compounds, or salts thereof. Isotopically labeled compounds or salts thereof have structures depicted by the formulas given herein except that one or more atoms are replaced by an atom having a selected atomic mass or mass number. Examples of isotopes that can be incorporated into compounds of the disclosure include isotopes of hydrogen, carbon, nitrogen, oxygen, phosphorous, fluorine and chlorine, such as, but not limited to $^2$H (deuterium, D), $^3$H (tritium), $^{11}$C, $^{13}$C, $^{14}$C, $^{15}$N, $^{18}$F, $^{31}$P, $^{32}$P, $^{35}$S, $^{36}$Cl and $^{125}$I. Various isotopically labeled compounds or salts thereof of the present disclosure, for example those into which radioactive isotopes such as $^3$H, $^{13}$C and $^{14}$C are incorporated. Such isotopically labeled compounds or salts thereof may be useful in metabolic studies, reaction kinetic studies, detection or imaging techniques, such as positron emission tomography (PET) or single-photon emission computed tomography (SPECT) including drug or substrate tissue distribution assays or in radioactive treatment of subjects (e.g. humans).

The disclosure also includes the compound of formula I and pharmaceutically acceptable salts thereof, in which from 1 to n hydrogens attached to a carbon atom is/are replaced by deuterium, in which n is the number of hydrogens in the molecule. Such compounds may exhibit increased resistance to metabolism and are thus useful for increasing the half-life of the compound of formula I, or pharmaceutically acceptable salts thereof when administered to a mammal. See, for example, Foster, "Deuterium Isotope Effects in Studies of Drug Metabolism", Trends Pharmacol. Sci. 5(12):524-527 (1984). Such compounds are synthesized by means well known in the art, for example by employing starting materials in which one or more hydrogens have been replaced by deuterium.

Deuterium labeled or substituted therapeutic compounds of the disclosure may have improved DMPK (drug metabolism and pharmacokinetics) properties, relating to distribution, metabolism and excretion (ADME). Substitution with heavier isotopes such as deuterium may afford certain therapeutic advantages resulting from greater metabolic stability, for example increased in vivo half-life, reduced dosage requirements and/or an improvement in therapeutic index. An $^{18}$F labeled compound may be useful for PET or SPECT studies. Isotopically labeled compounds of this disclosure and prodrugs thereof can generally be prepared by carrying out the procedures disclosed in the schemes or in the examples and preparations described below by substituting a readily available isotopically labeled reagent for a non-isotopically labeled reagent. It is understood that deuterium in this context is regarded as a substituent in the compound of formula I and pharmaceutically acceptable salts thereof.

The concentration of such a heavier isotope, specifically deuterium, may be defined by an isotopic enrichment factor. In the compounds of this disclosure any atom not specifically designated as a particular isotope is meant to represent any stable isotope of that atom. Unless otherwise stated, when a position is designated specifically as "H" or "hydrogen", the position is understood to have hydrogen at its natural abundance isotopic composition. Accordingly, in the compounds or salts thereof of this disclosure any atom specifically designated as a deuterium (D) is meant to represent deuterium.

Pharmaceutically Acceptable Salts

In some embodiments of the methods described herein, a pharmaceutically acceptable salt of the compound of formula I is administered to the subject (e.g., a human).

As used herein, by "pharmaceutically acceptable" refers to a material that is not biologically or otherwise undesirable, e.g., the material may be incorporated into a pharmaceutical composition administered to a patient without causing any significant undesirable biological effects or interacting in a deleterious manner with any of the other components of the composition in which it is contained. Pharmaceutically acceptable vehicles (e.g., carriers, adjuvants, and/or other excipients) have preferably met the required standards of toxicological and manufacturing testing and/or are included on the Inactive Ingredient Guide prepared by the U.S. Food and Drug administration.

"Pharmaceutically acceptable salts" include, for example, salts with inorganic acids and salts with an organic acid. Examples of salts may include hydrochlorate, phosphate, diphosphate, hydrobromate, sulfate, sulfinate, nitrate, malate, maleate, fumarate, tartrate, succinate, citrate, acetate, lactate, mesylate, p-toluenesulfonate, 2-hydroxyethylsulfonate, benzoate, salicylate, stearate, and alkanoate (such as acetate, $HOOC-(CH_2)_n-COOH$ where n is 0-4). In addition, if the compounds described herein are obtained as an acid addition salt, the free base can be obtained by basifying a solution of the acid salt. Conversely, if the product is a free base, an addition salt, particularly a pharmaceutically acceptable addition salt, may be produced by dissolving the free base in a suitable organic solvent and treating the solution with an acid, in accordance with conventional procedures for preparing acid addition salts from base compounds. Those skilled in the art will recognize various synthetic methodologies that may be used to prepare nontoxic pharmaceutically acceptable addition salts.

Pharmaceutical Compositions

In some embodiments of the methods described herein, the compound of formula I, or a pharmaceutically acceptable salt, is present in a pharmaceutical composition comprising the compound of formula I, or a pharmaceutically acceptable salt, and at least one pharmaceutically acceptable vehicle. Pharmaceutically acceptable vehicles may include pharmaceutically acceptable carriers, adjuvants and/or other excipients, and other ingredients can be deemed pharmaceutically acceptable insofar as they are compatible with other ingredients of the formulation and not deleterious to the recipient thereof.

The pharmaceutical compositions described herein can be manufactured using any conventional method, e.g., mixing, dissolving, granulating, dragee-making, levigating, emulsifying, encapsulating, entrapping, melt-spinning, spray-drying, or lyophilizing processes. An optimal pharmaceutical formulation can be determined by one of skill in the art depending on the route of administration and the desired dosage. Such formulations can influence the physical state, stability, rate of in vivo release, and rate of in vivo clearance of the administered agent. Depending on the condition being treated, these pharmaceutical compositions can be formulated and administered systemically or locally.

The term "carrier" refers to diluents, disintegrants, precipitation inhibitors, surfactants, glidants, binders, lubricants, and other excipients and vehicles with which the compound is administered. Carriers are generally described herein and also in "Remington's Pharmaceutical Sciences" by E. W. Martin. Examples of carriers include, but are not limited to, aluminum monostearate, aluminum stearate, carboxymethylcellulose, carboxymethylcellulose sodium, crospovidone, glyceryl isostearate, glyceryl monostearate, hydroxyethyl cellulose, hydroxyethyl cellulose, hydroxymethyl cellulose, hydroxyoctacosanyl hydroxystearate, hydroxypropyl cellulose, hydroxypropyl cellulose, hydroxypropyl methylcellulose, lactose, lactose monohydrate, magnesium stearate, mannitol, microcrystalline cellulose, poloxamer 124, poloxamer 181, poloxamer 182, poloxamer 188, poloxamer 237, poloxamer 407, povidone, silicon dioxide, colloidal silicon dioxide, silicone, silicone adhesive 4102, and silicone emulsion. It should be understood, however, that the carriers selected for the pharmaceutical compositions, and the amounts of such carriers in the composition, may vary depending on the method of formulation (e.g., dry granulation formulation, solid dispersion formulation).

The term "diluent" generally refers to a substance that are used to dilute the compound of interest prior to delivery. Diluents can also serve to stabilize compounds. Examples of diluents may include starch, saccharides, disaccharides, sucrose, lactose, polysaccharides, cellulose, cellulose ethers, hydroxypropyl cellulose, sugar alcohols, xylitol, sorbitol, maltitol, microcrystalline cellulose, calcium or sodium carbonate, lactose, lactose monohydrate, dicalcium phosphate, cellulose, compressible sugars, dibasic calcium phosphate dehydrate, mannitol, microcrystalline cellulose, and tribasic calcium phosphate.

The term "disintegrant" generally refers to a substance which, upon addition to a solid preparation, facilitates its break-up or disintegration after administration and permits the release of an active ingredient as efficiently as possible to allow for its rapid dissolution. Examples of disintegrants may include maize starch, sodium starch glycolate, croscarmellose sodium, crospovidone, microcrystalline cellulose, modified corn starch, sodium carboxymethyl starch, povidone, pregelatinized starch, and alginic acid.

The term "precipitation inhibitors" generally refers to a substance that prevents or inhibits precipitation of the active agent from a supersaturated solution. One example of a precipitation inhibitor includes hydroxypropylmethylcellulose (HPMC).

The term "surfactants" generally refers to a substance that lowers the surface tension between a liquid and a solid that could improve the wetting of the active agent or improve the solubility of the active agent. Examples of surfactants include poloxamer and sodium lauryl sulfate.

The term "glidant" generally refers to substances used in tablet and capsule formulations to improve flow-properties during tablet compression and to produce an anti-caking effect. Examples of glidants may include colloidal silicon dioxide, talc, fumed silica, starch, starch derivatives, and bentonite.

The term "binder" generally refers to any pharmaceutically acceptable film which can be used to bind together the active and inert components of the carrier together to maintain cohesive and discrete portions. Examples of binders may include hydroxypropylcellulose, hydroxypropylmethylcellulose, povidone, copovidone, and ethyl cellulose.

The term "lubricant" generally refers to a substance that is added to a powder blend to prevent the compacted powder mass from sticking to the equipment during the tableting or encapsulation process. A lubricant can aid the ejection of the tablet form the dies, and can improve powder flow. Examples of lubricants may include magnesium stearate, stearic acid, silica, fats, calcium stearate, polyethylene glycol, sodium stearyl fumarate, or talc; and solubilizers such as fatty acids including lauric acid, oleic acid, and $C_8/C_{10}$ fatty acid.

Methods of Treatment

Provided herein are methods for using a compound of formula I, or a pharmaceutically acceptable salt thereof, to selectively or specifically inhibit Syk activity therapeutically or prophylactically. The method comprises administering a compound of formula I, or a pharmaceutically acceptable salt thereof, or a pharmaceutical composition thereof, to a subject (e.g., a human) in need thereof in an amount sufficient to inhibit Syk activity. The method can be employed to treat subjects (e.g., humans) suffering from, or subject to, a condition whose symptoms or pathology is mediated by Syk expression or activity.

"Treatment" or "treating" is an approach for obtaining beneficial or desired results including clinical results. Beneficial or desired clinical results may include one or more of the following:

(i) decreasing one more symptoms resulting from the disease;

(ii) diminishing the extent of the disease and/or stabilizing the disease (e.g., delaying the worsening of the disease);

(iii) delaying the spread (e.g., metastasis) of the disease;

(iv) delaying or slowing the recurrence of the disease and/or the progression of the disease;

(v) ameliorating the disease state and/or providing a remission (whether partial or total) of the disease and/or decreasing the dose of one or more other medications required to treat the disease;

(vi) increasing the quality of life, and/or (vii) prolonging survival.

"Delaying" the development of a disease or condition means to defer, hinder, slow, retard, stabilize, and/or postpone development of the disease or condition. This delay can be of varying lengths of time, depending on the history of the disease or condition, and/or subject being treated. A method that "delays" development of a disease or condition is a method that reduces probability of disease or condition development in a given time frame and/or reduces the extent of the disease or condition in a given time frame, when compared to not using the method. Such comparisons are typically based on clinical studies, using a statistically significant number of subjects. Disease or condition development can be detectable using standard methods, such as routine physical exams, mammography, imaging, or biopsy. Development may also refer to disease or condition progression that may be initially undetectable and includes occurrence, recurrence, and onset.

The compound of formula I, or a pharmaceutically acceptable salt thereof, may, in some embodiments, be administered to a subject (e.g., a human) who is at risk or has a family history of the disease or condition.

The term "inhibition" indicates a decrease in the baseline activity of a biological activity or process. "Inhibition of activity of Syk activity" refers to a decrease in activity of Syk as a direct or indirect response to the presence of the compound of formula I, or a pharmaceutically acceptable salt thereof, relative to the activity of Syk in the absence of such compound or a pharmaceutically acceptable salt thereof. In some embodiments, the inhibition of Syk activity may be compared in the same subject prior to treatment, or other subjects not receiving the treatment.

Diseases

In some embodiments, the compound of formula I, or a pharmaceutically acceptable salt thereof, or a pharmaceutical composition thereof, is used in the treatment of cancer. In certain embodiments, the compound of formula I, or a pharmaceutically acceptable salt thereof, is used in the treatment of a hematologic malignancy. In some embodiments, the compound of formula I, or a pharmaceutically acceptable salt thereof, inhibits the growth or proliferation of cancer cells of hematopoietic origin. In some embodiments, the cancer cells are of lymphoid origin, and in certain embodiments, the cancer cells are related to or derived from B lymphocytes or B lymphocyte progenitors.

Hematologic malignancies amenable to treatment using the method disclosed in the present disclosure include, without limitation, lymphomas (e.g., malignant neoplasms of lymphoid and reticuloendothelial tissues, such as Burkitt's lymphoma, Hodgkins' lymphoma, non-Hodgkins' lymphomas, lymphocytic lymphomas); multiple myelomas; leukemias (e.g., lymphocytic leukemias, chronic myeloid (myelogenous) leukemias). Other cancer cells, of hematopoietic origin or otherwise, that express Syk also can be treated by administration of the polymorphs and compositions thereof described herein.

In particular embodiments, the hematologic malignancy is leukemia or lymphoma. In certain embodiments, the hematologic malignancy is acute lymphocytic leukemia (ALL), acute myeloid leukemia (AML), chronic lymphocytic leukemia (CLL), small lymphocytic lymphoma (SLL), myelodysplastic syndrome (MDS), myeloproliferative disease (MPD), chronic myeloid leukemia (CML), multiple myeloma (MM), non-Hodgkin's lymphoma (NHL), indolent non-Hodgkin's lymphoma (iNHL), refractory iNHL, mantle cell lymphoma (MCL), follicular lymphoma (FL), Waldestrom's macroglobulinemia (WM), T-cell lymphoma, B-cell lymphoma, diffuse large B-cell lymphoma (DLBCL), lymphoplasmacytic lymphoma (LPL), and marginal zone lymphoma (MZL).

In one embodiment, the cancer is T-cell acute lymphoblastic leukemia (T-ALL), or B-cell acute lymphoblastic leukemia (B-ALL). In another embodiment, the cancer is chronic lymphocytic leukemia (CLL). In yet another embodiment, the cancer is non-Hodgkin's lymphoma (NHL). In one embodiment, the NHL is diffuse large B-cell lymphoma (DLBCL), mantle cell lymphoma (MCL), follicular lymphoma (FL), small lymphocytic lymphoma (SLL), lymphoplasmacytic lymphoma (LPL), and marginal zone lymphoma (MZL). In one embodiment, the cancer is indolent non-Hodgkin's lymphoma (iNHL).

In yet another aspect, provided are methods of treating a subject (e.g., a human) having a Syk-mediated disorder by administering a compound of formula I, or a pharmaceutically acceptable salt thereof, or a pharmaceutical composition thereof, to the subject. Provided are also methods of modulating Syk in a subject (e.g., a human) by administering a compound of formula I, or a pharmaceutically acceptable salt thereof, or a pharmaceutical composition thereof, to the subject.

In any of the methods described herein, the compound of formula I, or a pharmaceutically acceptable salt thereof, may be administered to the individual as a unit dosage, for example in the form of a tablet.

Any of the methods of treatment provided herein may be used to treat cancer at an advanced stage. Any of the methods of treatment provided herein may be used to treat cancer at locally advanced stage. Any of the methods of treatment provided herein may be used to treat early stage cancer. Any of the methods of treatment provided herein may be used to treat cancer in remission. In some of the embodiments of any of the methods of treatment provided herein, the cancer has reoccurred after remission. In some embodiments of any of the methods of treatment provided herein, the cancer is progressive cancer.

Subjects

Any of the methods of treatment provided may be used to treat a subject who has been diagnosed with or is suspected of having cancer. "Subject" refers to an animal, such as a mammal (including a human), that has been or will be the object of treatment, observation or experiment. The methods described herein may be useful in human therapy and/or veterinary applications. In some embodiments, the subject is a mammal. In one embodiment, the subject is a human.

In some of the embodiments of any of the methods provided herein, the subject is a human who is at risk of developing a cancer (e.g., a human who is genetically or otherwise predisposed to developing a cancer) and who has or has not been diagnosed with the cancer. As used herein, an "at risk" subject is a subject who is at risk of developing cancer (e.g., a hematologic malignancy). The subject may or may not have detectable disease, and may or may not have displayed detectable disease prior to the treatment methods described herein. An at risk subject may have one or more so-called risk factors, which are measurable parameters that correlate with development of cancer, such as described herein. A subject having one or more of these risk factors has a higher probability of developing cancer than an individual without these risk factor(s).

These risk factors may include, for example, age, sex, race, diet, history of previous disease, presence of precursor disease, genetic (e.g., hereditary) considerations, and environmental exposure. In some embodiments, a subject at risk for cancer includes, for example, a subject whose relatives have experienced this disease, and those whose risk is determined by analysis of genetic or biochemical markers. Prior history of having cancer may also be a risk factor for instances of cancer recurrence.

Provided herein are methods for treating a subject (e.g., a human) who is at "very high risk" or "high risk" for cancer (e.g., a hematologic malignancy). Such subjects may be identified by the present of certain genetic deletions and/or mutations. In one aspect, a very high risk subject is a human who has a 17p deletion, a TP53 mutation, or a combination thereof. In one aspect, a high risk subject is a human who has a NOTCH1 mutation, a SF3B1 mutation, a 11q deletion, or any combination thereof. Thus, it is understood that methods of treatment as detailed herein may, in some instances, employ selecting a subject who is at very high risk or at high risk for cancer by detecting the presence or absence of one or more 17p deletion, a TP53 mutation, a NOTCH1 mutation, a SF3B1 mutation, a 11q deletion, or any combination thereof.

Provided herein are also methods for treating a subject (e.g., a human) who exhibits one or more symptoms associated with cancer (e.g., a hematologic malignancy). In some embodiments, the subject is at an early stage of cancer. In other embodiments, the subject is at an advanced stage of cancer.

Provided herein are also methods for treating a subject (e.g., a human) who is undergoing one or more standard therapies for treating cancer (e.g., a hematologic malignancy), such as chemotherapy, radiotherapy, immunotherapy, and/or surgery. Thus, in some foregoing embodiments, the compound of formula I, or a pharmaceutically acceptable salt thereof, administered before, during, or after administration of chemotherapy, radiotherapy, immunotherapy, and/or surgery.

In certain embodiments, the subject may be a human who is (i) refractory to at least one anti-cancer therapy, or (ii) in relapse after treatment with at least one anti-cancer therapy, or both (i) and (ii). In some of embodiments, the subject is refractory to at least two, at least three, or at least four anti-cancer therapy (including, for example, standard or experimental chemotherapies).

In certain embodiments, the subject is refractory to at least one, at least two, at least three, or at least four anti-cancer therapy (including, for example, standard or experimental chemotherapy) selected from fludarabine, rituximab, obinutuzumab, alkylating agents, alemtuzumab and other chemotherapy treatments such as CHOP (cyclophosphamide, doxorubicin, vincristine, prednisone); R-CHOP (rituximab-CHOP); hyperCVAD (hyperfractionated cyclophosphamide, vincristine, doxorubicin, dexamethasone, methotrexate, cytarabine); R-hyperCVAD (rituximab-hyperCVAD); FCM (fludarabine, cyclophosphamide, mitoxantrone); R-FCM (rituximab, fludarabine, cyclophosphamide, mitoxantrone); bortezomib and rituximab; temsirolimus and rituximab; temsirolimus and Velcade®; Iodine-131 tositumomab (Bexxar®) and CHOP; CVP (cyclophosphamide, vincristine, prednisone); R-CVP (rituximab-CVP); ICE (iphosphamide, carboplatin, etoposide); R-ICE (rituximab-ICE); FCR (fludarabine, cyclophosphamide, rituximab); FR (fludarabine, rituximab); and D.T. PACE (dexamethasone, thalidomide, cisplatin, Adriamycin®, cyclophosphamide, etoposide).

Other examples of chemotherapy treatments (including standard or experimental chemotherapies) are described below. In addition, treatment of certain lymphomas is reviewed in Cheson, B. D., Leonard, J. P., "Monoclonal Antibody Therapy for B-Cell Non-Hodgkin's Lymphoma" *The New England Journal of Medicine* 2008, 359(6), p. 613-626; and Wierda, W. G., "Current and Investigational Therapies for Patients with CLL" *Hematology* 2006, p. 285-294. Lymphoma incidence patterns in the United States is profiled in Morton, L. M., et al. "Lymphoma Incidence Patterns by WHO Subtype in the United States, 1992-2001" *Blood* 2006, 107(1), p. 265-276.

For example, treatment of non-Hodgkin's lymphomas (NHL), especially of B-cell origin, include the use of monoclonal antibodies, standard chemotherapy approaches (e.g., CHOP, CVP, FCM, MCP, and the like), radioimmunotherapy, and combinations thereof, especially integration of an antibody therapy with chemotherapy. Examples of unconjugated monoclonal antibodies for Non-Hodgkin's lymphoma/B-cell cancers include rituximab, alemtuzumab, human or humanized anti-CD20 antibodies, lumiliximab, anti-TRAIL, bevacizumab, galiximab, epratuzumab, SGN-40, and anti-CD74. Examples of experimental antibody agents used in treatment of Non-Hodgkin's lymphoma/B-cell cancers include ofatumumab, ha20, PRO131921, alemtuzumab, galiximab, SGN-40, CHIR-12.12, epratuzumab, lumiliximab, apolizumab, milatuzumab, and bevacizumab. Examples of standard regimens of chemotherapy for Non-Hodgkin's lymphoma/B-cell cancers include CHOP (cyclophosphamide, doxorubicin, vincristine, prednisone), FCM (fludarabine, cyclophosphamide, mitoxantrone), CVP (cyclophosphamide, vincristine and prednisone), MCP (mitoxantrone, chlorambucil, and prednisolone), R-CHOP (rituximab plus CHOP), R-FCM (rituximab plus FCM), R-CVP (rituximab plus CVP), and R-MCP (R-MCP). Examples of radioimmunotherapy for Non-Hodgkin's lymphoma/B-cell cancers include yttrium-90-labeled ibritumomab tiuxetan, and iodine-131-labeled tositumomab.

In another example, therapeutic treatments for mantle cell lymphoma (MCL) include combination chemotherapies such as CHOP (cyclophosphamide, doxorubicin, vincristine, prednisone), hyperCVAD (hyperfractionated cyclophosphamide, vincristine, doxorubicin, dexamethasone, methotrexate, cytarabine) and FCM (fludarabine, cyclophosphamide, mitoxantrone). In addition, these regimens can be supplemented with the monoclonal antibody rituximab (Rituxan®) to form combination therapies R-CHOP, hyperCVAD-R, and R-FCM. Other approaches include combining any of the abovementioned therapies with stem cell transplantation or treatment with ICE (iphosphamide, carboplatin and etoposide). Other approaches to treating mantle cell lymphoma include immunotherapy such as using monoclonal antibodies like Rituximab (Rituxan®). Rituximab can be used for treating indolent B-cell cancers, including marginal-zone lymphoma, WM, CLL and small lymphocytic lymphoma. A combination of Rituximab and chemotherapy agents is especially effective. A modified approach is radioimmunotherapy, wherein a monoclonal antibody is combined with a radioisotope particle, such as Iodine-131 tositumomab (Bexxar®) and Yttrium-90 ibritumomab tiuxetan (Zevalin®). In another example, Bexxar® is used in sequential treatment with CHOP. Another immunotherapy example includes using cancer vaccines, which is based upon the genetic makeup of an individual patient's tumor. A lymphoma vaccine example is GTOP-99 (MyVax®). Yet other approaches to treating mantle cell lymphoma include autologous stem cell transplantation coupled with high-dose chemotherapy, or treating mantle cell lymphoma include administering proteasome inhibitors, such as Velcade® (bortezomib or PS-341), or antiangiogenesis agents, such as thalidomide, especially in combination with Rituxan®. Another treatment approach is administering drugs that lead to the degradation of Bcl-2 protein and increase cancer cell sensitivity to chemotherapy, such as oblimersen (Genasense) in combination with other chemotherapeutic agents. Another treatment approach includes administering mTOR inhibitors, which can lead to inhibition of cell growth and even cell death; a non-limiting example is Temsirolimus (CCI-779), and Temsirolimus in combination with Rituxan®, Velcade® or other chemotherapeutic agents.

Other recent therapies for MCL have been disclosed (*Nature Reviews*; Jares, P. 2007). Such examples include Flavopiridol, PD0332991, R-roscovitine (Selicilib, CYC202), Styryl sulphones, Obatoclax (GX15-070), TRAIL, Anti-TRAIL DR4 and DR5 antibodies, Temsirolimus (CCI-779), Everolimus (RAD001), BMS-345541, Curcumin, Vorinostat (SAHA), Thalidomide, Ienalidomide (Revlimid®, CC-5013), and Geldanamycin (17-AAG).

Examples of other therapeutic agents used to treat Waldenstrom's Macroglobulinemia (WM) include perifosine, bortezomib (Velcade®), rituximab, sildenafil citrate (Viagra®), CC-5103, thalidomide, epratuzumab (hLL2-anti-CD22 humanized antibody), simvastatin, enzastaurin, campath-1H, dexamethasone, DT PACE, oblimersen, antineoplaston A10, antineoplaston AS2-1, alemtuzumab, beta alethine, cyclophosphamide, doxorubicin hydrochloride, prednisone, vincristine sulfate, fludarabine, filgrastim, melphalan, recombinant interferon alfa, carmustine, cisplatin, cyclophosphamide, cytarabine, etoposide, melphalan, dolastatin 10, indium In 111 monoclonal antibody MN-14, yttrium Y 90 humanized epratuzumab, anti-thymocyte globulin, busulfan, cyclosporine, methotrexate, mycophenolate mofetil, therapeutic allogeneic lymphocytes, Yttrium Y 90 ibritumomab tiuxetan, sirolimus, tacrolimus, carboplatin, thiotepa, paclitaxel, aldesleukin, recombinant interferon alfa, docetaxel, ifosfamide, mesna, recombinant interleukin-12, recombinant interleukin-11, Bcl-2 family protein inhibitor ABT-263, denileukin diftitox, tanespimycin, everolimus, pegfilgrastim, vorinostat, alvocidib, recombinant flt3 ligand, recombinant human thrombopoietin, lymphokine-activated killer cells, amifostine trihydrate, aminocamptothecin, irinotecan hydrochloride, caspofungin acetate, clofarabine, epoetin alfa, nelarabine, pentostatin, sargramostim, vinorelbine ditartrate, WT-1 analog peptide vaccine, WT1 126-134 peptide vaccine, fenretinide, ixabepilone, oxaliplatin, monoclonal antibody CD19, monoclonal antibody CD20, omega-3 fatty acids, mitoxantrone hydrochloride, octreotide acetate, tositumomab and iodine I-131 tositumomab, motexafin gadolinium, arsenic trioxide, tipifarnib, autologous human tumor-derived HSPPC-96, veltuzumab, bryostatin 1, and PEGylated liposomal doxorubicin hydrochloride, and any combination thereof.

Examples of therapeutic procedures used to treat WM include peripheral blood stem cell transplantation, autologous hematopoietic stem cell transplantation, autologous bone marrow transplantation, antibody therapy, biological therapy, enzyme inhibitor therapy, total body irradiation, infusion of stem cells, bone marrow ablation with stem cell support, in vitro-treated peripheral blood stem cell transplantation, umbilical cord blood transplantation, immunoenzyme technique, pharmacological study, low-LET cobalt-60 gamma ray therapy, bleomycin, conventional surgery, radiation therapy, and nonmyeloablative allogeneic hematopoietic stem cell transplantation.

Examples of other therapeutic agents used to treat diffuse large B-cell lymphoma (DLBCL) drug therapies (*Blood* 2005 Abramson, J.) include cyclophosphamide, doxorubicin, vincristine, prednisone, anti-CD20 monoclonal antibodies, etoposide, bleomycin, many of the agents listed for Waldenstrom's, and any combination thereof, such as ICE and R-ICE.

Examples of other therapeutic agents used to treat chronic lymphocytic leukemia (CLL) (Spectrum, 2006, Fernandes, D.) include Chlorambucil (Leukeran®), Cyclophosphamide (Cyloxan®, Endoxan®, Endoxana®, Cyclostin), Fludarabine (Fludara®), Pentstatin (Nipent®), Cladribine (Leustarin®), Doxorubicin (Adriamycin®, Adriblastine®), Vincristine (Oncovin®), Prednisone, Prednisolone, Alemtuzumab (Campath®, MabCampath®), many of the agents listed for Waldenstrom's, and combination chemotherapy and chemoimmunotherapy, including the common combination regimen: CVP (cyclophosphamide, vincristine, prednisone); R-CVP (rituximab-CVP); ICE (iphosphamide, carboplatin, etoposide); R-ICE (rituximab-ICE); FCR (fludarabine, cyclophosphamide, rituximab); and FR (fludarabine, rituximab).

In yet another aspect, provided is a method of sensitizing a subject (e.g., a human) who is (i) refractory to at least one chemotherapy treatment, or (ii) in relapse after treatment with chemotherapy, or both (i) and (ii), wherein the method comprises administering a compound of formula I, or a pharmaceutically acceptable salt thereof, or a pharmaceutical composition thereof, to the subject. A subject who is sensitized is a subject who is responsive to the treatment involving administration of the compound of formula I, or a pharmaceutically acceptable salt thereof, or who has not developed resistance to such treatment.

Monotherapy and Combination Therapies

Monotherapy

In one aspect, the compound of formula I, or a pharmaceutically acceptable salt thereof, is administered as a monotherapy to the subject (e.g., a human). Provided herein are methods of treatment in which the compound of formula I, or a pharmaceutically acceptable salt thereof, administered to a subject (e.g., a human) is the only anti-cancer therapy administered to the subject. Provided herein are methods of treatment in which the compound of formula I, or a pharmaceutically acceptable salt thereof, administered to a subject (e.g., a human), wherein the subject is not undergoing any other anti-cancer treatments. In one variation, the subject is not undergoing any other anti-cancer treatments using one or more PI3K inhibitors. Such PI3K inhibitors may include, in certain embodiments, Compounds A, B and C, whose structures are provided below.

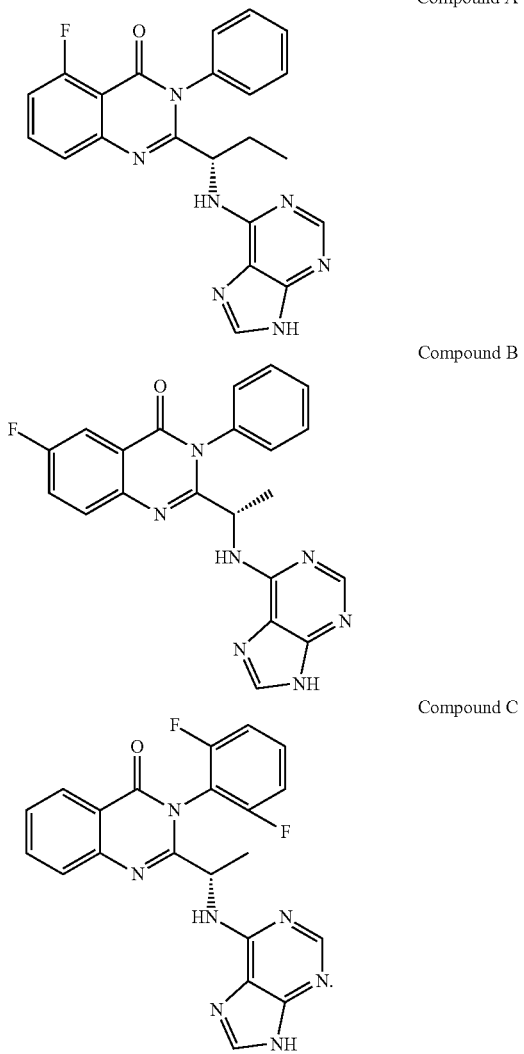

Compound A

Compound B

Compound C

In one variation, the subject is not undergoing any other anti-cancer treatments using Compound A, or a pharmaceutically acceptable salt thereof. In another variation, the subject is not undergoing any other anti-cancer treatments using Compound B, or a pharmaceutically acceptable salt thereof. In yet another variation, the subject is not undergoing any other anti-cancer treatments using Compound C, or a pharmaceutically acceptable salt thereof.

In some embodiments where the compound of formula I, or a pharmaceutically acceptable salt thereof, is administered as a monotherapy to the subject, the subject may be a human who is (i) refractory to at least one anti-cancer therapy, or (ii) in relapse after treatment with at least one anti-cancer therapy, or both (i) and (ii). In some of embodiments, the subject is refractory to or in relapse after at least two, at least three, or at least four anti-cancer therapy (including, for example, standard or experimental chemotherapies). For example, in certain embodiments, the subject may be a human who is (i) refractory to a therapy using an anti-CD20 antibody, an alkylating agent (e.g., bendamustine), a purine analog (e.g., fludarabine), an anthracycline, or any combination thereof; (ii) in relapse after treatment with an anti-CD20 antibody, an alkylating agent (e.g., bendamustine), a purine analog (e.g., fludarabine), an anthracycline, or any combination thereof, or both (i) and (ii).

A human subject who is refractory to at least one anti-cancer therapy and/or is in relapse after treatment with at least one anti-cancer therapy, as described above, may have undergone one or more prior therapies. In some embodiments, such subjects have undergone one, two, three, or four, or at least one, at least two, at least three, at least four, or at least five, or between one and ten, between one and nine, between one and eight, between one and seven, between one and six, between one and five, between one and four, or between one and three anti-cancer therapies prior to treatment using the methods described herein (e.g., prior to the administration of the compound of formula I, or a pharmaceutically acceptable salt thereof, as a monotherapy).

It should be understood that when a subject (e.g. a human) is treated with the compound of formula I, or a pharmaceutically acceptable salt thereof, as a monotherapy, the subject may also undergo one or more other therapies that are not anti-cancer therapies.

In yet other embodiments where the compound of formula I, or a pharmaceutically acceptable salt thereof, is administered as a monotherapy to the subject, the subject may have a 17p deletion, a TP53 mutation, a NOTCH1 mutation, a SF3B1 mutation, a 11q deletion, or any combination thereof. In one embodiment where the compound of formula I, or a pharmaceutically acceptable salt thereof, is administered as a monotherapy to the subject, the subject has a 17p deletion, a TP53 mutation, or a combination thereof. In another embodiment where the compound of formula I, or a pharmaceutically acceptable salt thereof, is administered as a monotherapy to the subject, the subject has a NOTCH1 mutation, a SF3B1 mutation, a 11q deletion, or any combination thereof.

Combination Therapies

Provided herein are also methods of treatment in which the compound of formula I, or a pharmaceutically acceptable salt thereof, administered to a subject (e.g., a human) is given to a subject (e.g., a human) in combination with one or more additional therapies, including one or more of the anti-cancer therapies described above. Thus, in some embodiments, the method for treating cancer in a subject (e.g., a human) in need thereof, comprises administering to the subject a therapeutically effective amount of a compound of formula I, or a pharmaceutically acceptable salt thereof, or a pharmaceutical composition thereof, together with one or more additional therapies, which can be useful for treating the cancer. The one or more additional therapies may involve the administration of one or more therapeutic agents.

In some embodiments, the one or more additional therapies involve the use of a phosphatidylinositol 3-kinase (PI3K) inhibitor, including for example, Compounds A, B and C, or a pharmaceutically acceptable salt of such compounds.

In other embodiments of the methods described above involving the use of the compound of formula I, or a pharmaceutically acceptable salt thereof, in combination with one or more additional therapies, the one or more additional therapies is other than a therapy using Compound A, Compound B, or Compound C, or a pharmaceutically acceptable salt of such compounds. In one embodiment of the methods described above involving the use of the compound of formula I, or a pharmaceutically acceptable salt thereof, in combination with one or more additional therapies, the one or more additional therapies is other than a therapy using Compound A, or a pharmaceutically acceptable salt thereof. In another embodiment of the methods described above involving the use of the compound of formula I, or a pharmaceutically acceptable salt thereof, in combination with one or more additional therapies, the one or more additional therapies is other than a therapy using Compound B, or a pharmaceutically acceptable salt thereof. In yet another embodiment of the methods described above involving the use of the compound of formula I, or a pharmaceutically acceptable salt thereof, in combination with one or more additional therapies, the one or more additional therapies is other than a therapy using Compound C, or a pharmaceutically acceptable salt thereof.

In other embodiments, the one or more additional therapeutic agent may be an inhibitors of lysyl oxidase-like 2 (LOXL2) and a substance that bind to LOXL2, including for example, a humanized monoclonal antibody (mAb) with an immunoglobulin IgG4 isotype directed against human LOXL2. An example of an antibody which may be used in the combination therapies herein includes simtuzumab.

In other embodiments, the one or more additional therapeutic agent may be an anti-inflammatory agent. Treatment with the one or more additional therapeutic agent may be prior to, concomitant with, or following treatment with the pharmaceutical composition described herein. In some embodiments, the pharmaceutical composition described herein is combined with another therapeutic agent in a single dosage form. Suitable antitumor therapeutics that may be used in combination with at least one chemical entity described herein include, but are not limited to, chemotherapeutic agents, for example mitomycin C, carboplatin, taxol, cisplatin, paclitaxel, etoposide, doxorubicin, or a combination comprising at least one of the foregoing chemotherapeutic agents. Radiotherapeutic antitumor agents may also be used, alone or in combination with chemotherapeutic agents.

The compound of formula I, or a pharmaceutically acceptable salt thereof, can be useful as chemosensitizing agents, and, thus, can be useful in combination with other chemotherapeutic drugs, in particular, drugs that induce apoptosis.

A method for increasing sensitivity of cancer cells to chemotherapy, comprising administering to a subject (e.g., human) undergoing chemotherapy a chemotherapeutic agent together with a compound of formula I, or a pharmaceutically acceptable salt thereof, or a pharmaceutical composition thereof, in an amount sufficient to increase the sensitivity of cancer cells to the chemotherapeutic agent is also provided herein. Examples of other chemotherapeutic drugs that can be used in combination with chemical entities described herein include topoisomerase I inhibitors camptothecin or topotecan), topoisomerase II inhibitors (e.g. daunomycin and etoposide), alkylating agents (e.g. cyclophosphamide, melphalan and BCNU), tubulin directed agents (e.g. taxol and vinblastine), and biological agents (e.g. antibodies such as anti CD20 antibody, IDEC 8, immunotoxins, and cytokines). In one embodiment of the method for increasing sensitivity of cancer cells to chemotherapy, the chemotherapeutic agent is other than Compound A, or a pharmaceutically acceptable salt thereof. In another embodiment of the method for increasing sensitivity of cancer cells to chemotherapy, the chemotherapeutic agent is other than Compound B, or a pharmaceutically acceptable salt thereof. In yet another embodiment of the method for increasing sensitivity of cancer cells to chemotherapy, the chemotherapeutic agent is other than Compound C, or a pharmaceutically acceptable salt thereof.

In some embodiments, the compound of formula I, or a pharmaceutically acceptable salt thereof, or a pharmaceutical composition thereof, is used in combination with Rituxan® (Rituximab) or other agents that work by selectively depleting CD20+ B-cells.

Included herein are methods of treatment in which the compound of formula I, or a pharmaceutically acceptable salt thereof, or a pharmaceutical composition thereof, is administered in combination with an anti-inflammatory agent. Anti-inflammatory agents include but are not limited to NSAIDs, non-specific and COX-2 specific cyclooxygenase enzyme inhibitors, gold compounds, corticosteroids, methotrexate, tumor necrosis factor receptor (TNF) receptors antagonists, immunosuppressants and methotrexate. Examples of NSAIDs include, but are not limited to ibuprofen, flurbiprofen, naproxen and naproxen sodium, diclofenac, combinations of diclofenac sodium and misoprostol, sulindac, oxaprozin, diflunisal, piroxicam, indomethacin, etodolac, fenoprofen calcium, ketoprofen, sodium nabumetone, sulfasalazine, tolmetin sodium, and hydroxychloroquine. Examples of NSAIDs also include COX-2 specific inhibitors (i.e., a compound that inhibits COX-2 with an IC50 that is at least 50-fold lower than the IC50 for COX-1) such as celecoxib, valdecoxib, lumiracoxib, etoricoxib and/or rofecoxib.

In a further embodiment, the anti-inflammatory agent is a salicylate. Salicylates include but are not limited to acetylsalicylic acid or aspirin, sodium salicylate, and choline and magnesium salicylates. The anti-inflammatory agent may also be a corticosteroid. For example, the corticosteroid may be chosen from cortisone, dexamethasone, methylprednisolone, prednisolone, prednisolone sodium phosphate, and prednisone. In some embodiments, the anti-inflammatory therapeutic agent is a gold compound such as gold sodium thiomalate or auranofin. In some embodiments, the anti-inflammatory agent is a metabolic inhibitor such as a dihydrofolate reductase inhibitor, such as methotrexate or a dihydroorotate dehydrogenase inhibitor, such as leflunomide.

In some embodiments, combinations in which at least one anti-inflammatory compound is an anti-C5 monoclonal antibody (such as eculizumab or pexelizumab), a TNF antagonist, such as entanercept, or infliximab, which is an anti-TNF alpha monoclonal antibody are used.

In some embodiments, combinations in which at least one therapeutic agent is an immunosuppressant compound such as methotrexate, leflunomide, cyclosporine, tacrolimus, azathioprine, or mycophenolate mofetil are used.

It should be understood that any combinations of the additional therapeutic agents described above may be used, as if each and every combination was individually listed. For example, in certain embodiments, the additional therapeutic agents include a PI3K inhibitor and a LOXL2 inhibitor.

Dosing Regimen and Modes of Administration

In the methods provided herein, the compound of formula I, or a pharmaceutically acceptable salt thereof, or a pharmaceutical composition thereof, is administered in a therapeutically effective amount to achieve its intended purpose. As used herein, a "therapeutically effective amount" is an amount sufficient to modulate Syk expression or activity, and thereby treat a subject (e.g., a human) suffering an indication, or to ameliorate or alleviate the existing symptoms of the indication. For example, a therapeutically effective amount may be an amount sufficient to decrease a symptom of a disease or condition responsive to inhibition of Syk activity.

Determination of a therapeutically effective amount is well within the capability of those skilled in the art, especially in light of the detailed disclosure provided herein. In some embodiments, a therapeutically effective amount of the compound of formula I, or a pharmaceutically acceptable salt thereof, may (i) reduce the number of cancer cells; (ii) reduce tumor size; (iii) inhibit, retard, slow to some extent, and preferably stop cancer cell infiltration into peripheral organs; (iv) inhibit (e.g., slow to some extent and preferably stop) tumor metastasis; (v) inhibit tumor growth; (vi) delay occurrence and/or recurrence of a tumor; and/or (vii) relieve to some extent one or more of the symptoms associated with the cancer. In various embodiments, the amount is sufficient to ameliorate, palliate, lessen, and/or delay one or more of symptoms of cancer.

The therapeutically effective amount may vary depending on the subject, and disease or condition being treated, the weight and age of the subject, the severity of the disease or condition, and the manner of administering, which can readily be determined by one or ordinary skill in the art.

The dosing regimen of the compound of formula I, or a pharmaceutically acceptable salt thereof, in the methods provided herein may vary depending upon the indication, route of administration, and severity of the condition, for example. Depending on the route of administration, a suitable dose can be calculated according to body weight, body surface area, or organ size. The final dosing regimen is determined by the attending physician in view of good medical practice, considering various factors that modify the action of drugs, e.g., the specific activity of the compound, the identity and severity of the disease state, the responsiveness of the patient, the age, condition, body weight, sex, and diet of the patient, and the severity of any infection. Additional factors that can be taken into account include time and frequency of administration, drug combinations, reaction sensitivities, and tolerance/response to therapy. Further refinement of the doses appropriate for treatment involving any of the formulations mentioned herein is done routinely by the skilled practitioner without undue experimentation, especially in light of the dosing information and assays disclosed, as well as the pharmacokinetic data observed in human clinical trials. Appropriate doses can be ascertained through use of established assays for determining concentration of the agent in a body fluid or other sample together with dose response data.

The formulation and route of administration chosen may be tailored to the individual subject, the nature of the condition to be treated in the subject, and generally, the judgment of the attending practitioner. For example, the therapeutic index of the compound of formula I, or a pharmaceutically acceptable salt thereof, may be enhanced by modifying or derivatizing the compound for targeted delivery to cancer cells expressing a marker that identifies the cells as such. For example, the compounds can be linked to an antibody that recognizes a marker that is selective or specific for cancer cells, so that the compounds are brought into the vicinity of the cells to exert their effects locally, as previously described. See e.g., Pietersz et al., Immunol. Rev., 129:57 (1992); Trail et al., Science, 261:212 (1993); and Rowlinson-Busza et al., Curr. Opin. Oncol., 4:1142 (1992).

Dosing Regimen

The therapeutically effective amount of the compound of formula I, or a pharmaceutically acceptable salt thereof, may be provided in a single dose or multiple doses to achieve the desired treatment endpoint. As used herein, "dose" refers to the total amount of an active ingredient (e.g., the compound of formula I, or a pharmaceutically acceptable salt thereof) to be taken each time by a subject (e.g., a human).

Exemplary doses of the compound of formula I, or a pharmaceutically acceptable salt thereof, for a human subject may be between about 0.01 mg to about 1800 mg, or between about 0.01 mg to about 1500 mg, or between about 10 mg to about 1500 mg, or between about 10 mg to about 1300 mg, or between about 10 mg to about 1000 mg, or between about 10 mg to about 800 mg, or between about 10 mg to about 600 mg, or between about 10 mg to about 300 mg, or between about 10 mg to about 200 mg, or between about 10 mg to about 100 mg, or between about 75 mg and 125 mg, or between about 50 mg and about 150 mg, or between about 100 mg to about 800 mg, or between about 100 mg to about 600 mg, or between about 100 mg to about 300 mg, or between about 100 mg to about 200 mg, or between about 150 mg and about 250 mg, or between about 175 mg and about 225 mg, or between about 200 mg to about 350 mg, or between about 250 mg to about 300 mg, or between about 250 mg and about 350 mg, or between about 275 mg and about 325 mg, or between about 200 mg to about 400 mg, or between about 350 mg and about 450 mg, or between about 375 mg and about 425 mg, or between about 400 mg to about 600 mg, or between about 450 mg and about 550 mg, or between about 400 mg to about 800 mg, or between about 600 mg or about 800 mg, or between about 550 mg and about 650 mg, or between about 650 mg and about 750 mg, or between about 750 mg and about 850 mg, or between about 850 mg and about 950 mg, or between about 950 mg and about 1050 mg, or between about 800 mg to about 1200 mg, or between about 1200 mg to about 1600, or between about 50 mg to about 200 mg, or about 25 mg, about 50 mg, about 75 mg, about 100 mg, about 125 mg, or about 150 mg, or about 175 mg, about 200 mg, about 250 mg, about 275 mg, about 300 mg, about 325 mg, about 350 mg, about 375 mg, about 400 mg, about 425 mg, about 450 mg, about 475 mg, about 500 mg, about 525 mg, about 550 mg, about 575 mg, about 600 mg, about 625 mg, about 650 mg, about 675 mg, about 700 mg, about 725 mg, or about 750 mg, about 775 mg, or about 800 mg, about 825 mg, or about 850 mg, about 875 mg, or about 900 mg, about 925 mg, or about 950 mg, about 975 mg, or about 1000 mg, or about 1100 mg, or about 1200 mg, or about 1300 mg, or about 1400 mg, or about 1500 mg, or about 1600 mg, or about 1800 mg. In one embodiment, the dose of the compound of formula I, or a pharmaceutically acceptable salt thereof is between about 600 mg and about 1,000 mg. In another embodiment, the dose of the compound of formula I, or a pharmaceutically acceptable salt thereof, administered to the subject in the methods provided herein is about 800 mg.

In other embodiments, the methods provided comprise continuing to treat the subject (e.g., a human) by administering the doses of the compound of formula I, or a pharmaceutically acceptable salt thereof, at which clinical efficacy is achieved or reducing the doses by increments to a level at which efficacy can be maintained. In a particular embodiment, the methods provided comprise administering to the subject (e.g., a human) an initial daily dose of 100 mg to 1000 mg of the compound of formula I, or a pharmaceutically acceptable salt thereof, and administering subsequent daily doses of the compound of formula I, or a pharmaceutically acceptable salt thereof, over at least 6 days, wherein each subsequent daily dose is increased by 50 mg to 400 mg. Thus, it should also be understood that the dose of the compound of formula I, or a pharmaceutically acceptable salt thereof, may be increased by increments until clinical efficacy is achieved. Increments of about 25 mg, about 50 mg, about 100 mg, or about 125 mg, or about 150 mg, or about 200 mg, or about 250 mg or about 300 mg can be used to increase the dose. The dose can be increased daily, every other day, two, three, four, five or six times per week, or once per week.

The frequency of dosing will depend on the pharmacokinetic parameters of the compound administered, the route of administration, and the particular disease treated. The dose and frequency of dosing may also depend on pharmacokinetic and pharmacodynamic, as well as toxicity and therapeutic efficiency data. For example, pharmacokinetic and pharmacodynamic information about the compound of formula I, or a pharmaceutically acceptable salt thereof, can be collected through preclinical in vitro and in vivo studies, later confirmed in humans during the course of clinical trials. Thus, for the compound of formula I, or a pharmaceutically acceptable salt thereof, used in the methods provided herein, a therapeutically effective dose can be estimated initially from biochemical and/or cell-based assays. Then, dosage can be formulated in animal models to achieve a desirable circulating concentration range that modulates Syk expression or activity. As human studies are conducted further information will emerge regarding the appropriate dosage levels and duration of treatment for various diseases and conditions.

Toxicity and therapeutic efficacy of the compound of formula I, or a pharmaceutically acceptable salt thereof, can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the "therapeutic index", which typically is expressed as the ratio $LD_{50}/ED_{50}$. Compounds that exhibit large therapeutic indices, i.e., the toxic dose is substantially higher than the effective dose, are preferred. The data obtained from such cell culture assays and additional animal studies can be used in formulating a range of dosage for human use. The doses of such compounds lies preferably within a range of circulating concentrations that include the $ED_{50}$ with little or no toxicity.

The administration of the compound of formula I, or a pharmaceutically acceptable salt thereof, may be administered under fed conditions. The term fed conditions or variations thereof refers to the consumption or uptake of food, in either solid or liquid forms, or calories, in any suitable form, before or at the same time when the compounds or pharmaceutical compositions thereof are administered. For example, the compound of formula I, or a pharmaceutically acceptable salt thereof, may be administered to the subject (e.g., a human) within minutes or hours of consuming calories (e.g., a meal). In some embodiments, the compound of formula I, or a pharmaceutically acceptable salt thereof, may be administered to the subject (e.g., a human) within 5-10 minutes, about 30 minutes, or about 60 minutes consuming calories.

Modes of Administration

The pharmaceutical compositions may be administered in either single or multiple doses by any of the accepted modes of administration of agents having similar utilities, for example as described in those patents and patent applications incorporated by reference, including rectal, buccal, intranasal and transdermal routes, by intra-arterial injection, intravenously, intraperitoneally, parenterally, intramuscularly, subcutaneously, orally, topically, as an inhalant, or via an impregnated or coated device such as a stent, for example, or an artery-inserted cylindrical polymer.

One mode for administration is parenteral, particularly by injection. The forms in which the compound of formula I, or a pharmaceutically acceptable salt thereof, may be incorporated for administration by injection include aqueous or oil suspensions, or emulsions, with sesame oil, corn oil, cottonseed oil, or peanut oil, as well as elixirs, mannitol, dextrose, or a sterile aqueous solution, and similar pharmaceutical vehicles. Aqueous solutions in saline may also conventionally be used for injection. Ethanol, glycerol, propylene glycol, liquid polyethylene glycol, and the like (and suitable mixtures thereof), cyclodextrin derivatives, and vegetable oils may also be employed. The proper fluidity can be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like.

Sterile injectable solutions are prepared by incorporating a compound according to the present disclosure in the required amount in the appropriate solvent with various other ingredients as enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof. In certain embodiments, for parenteral administration, sterile injectable solutions are prepared containing a therapeutically effective amount, e.g., 0.1 to 1000 mg, of the compound of formula I, or a pharmaceutically acceptable salt thereof. It will be understood, however, that the amount of the compound actually administered usually will be determined by a physician, in the light of the relevant circumstances, including the condition to be treated, the chosen route of administration, the actual compound administered and its relative activity, the age, weight, and response of the individual patient, the severity of the patient's symptoms, and the like.

Oral administration is another route for administration of the compound of formula I, or a pharmaceutically acceptable salt thereof. Administration may be via capsule or a tablet, including enteric coated tablets, or the like. In making the pharmaceutical compositions that include the compound of formula I, or a pharmaceutically acceptable salt thereof, the active ingredient is usually diluted by an excipient and/or enclosed within such a carrier that can be in the form of a capsule, sachet, paper or other container. When the excipient serves as a diluent, it can be in the form of a solid, semi-solid, or liquid material (as above), which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing, for example, up to 10% by weight of the active compound, soft and hard gelatin capsules, sterile injectable solutions, and sterile packaged powders.

Some examples of suitable excipients in an oral formulation include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, sterile water, syrup, and methyl cellulose. The formulations can additionally include: lubricating agents such as talc, magnesium stearate, and mineral oil; wetting agents; emulsifying and suspending agents; preserving agents such as methyl and propylhydroxy-benzoates; sweetening agents; and flavoring agents.

The pharmaceutical compositions described herein can be formulated so as to provide quick, sustained or delayed release of the active ingredient after administration to the patient by employing procedures known in the art. Controlled release drug delivery systems for oral administration include osmotic pump systems and dissolutional systems containing polymer-coated reservoirs or drug-polymer matrix formulations. Examples of controlled release systems are given in U.S. Pat. Nos. 3,845,770; 4,326,525; 4,902,514; and 5,616,345. Another formulation for use in the methods of the present disclosure employs transdermal delivery devices (patches). Such transdermal patches may be used to provide continuous or discontinuous infusion of the compounds of the present disclosure in controlled amounts. The construction and use of transdermal patches for the delivery of pharmaceutical agents is well known in the art. See, e.g., U.S. Pat. Nos. 5,023,252, 4,992,445 and 5,001,139. Such patches may be constructed for continuous, pulsatile, or on demand delivery of pharmaceutical agents.

In some embodiments, the compositions described herein are formulated in a unit dosage form. The term "unit dosage forms" refers to physically discrete units suitable as unitary dosages for human subjects, each unit containing a predetermined quantity of active material calculated to produce the desired therapeutic effect, in association with a suitable pharmaceutical excipient (e.g., a tablet, capsule, ampoule).

In other embodiments, the compound of formula I, or a pharmaceutically acceptable salt thereof, or a pharmaceutical composition thereof, is administered orally at a unit dosage of about 50 mg, about 100 mg, about 150 mg, about 200 mg, about 250 mg, about 300 mg, about 350 mg, about 400 mg, about 450 mg, about 500 mg, about 550 mg, about 600 mg, about 650 mg, about 700 mg, about 800 mg, about 900 mg, about 1100 mg, about 1200 mg, about 1300 mg, about 1400 mg, about 1500 mg, or about 1600 mg, about 1700 mg, or about 1800 mg. In other embodiments, the compound of formula I, or a pharmaceutically acceptable salt thereof, is administered orally at a unit dosage of about 200 mg, about 600 mg, or about 800 mg, or about 900 mg, or about 1200 mg. In some embodiments, the compound of formula I, or a pharmaceutically acceptable salt thereof, or a pharmaceutical composition thereof, is administered orally at a unit dosage of about 200 mg, or about 800 mg.

The dosages for oral administration described above may be administered once daily or twice daily (BID). For example, in certain embodiments, the compound of formula I, or a pharmaceutically acceptable salt thereof, or a pharmaceutical composition thereof, is administered orally at a unit dosage of about 50 mg BID, about 100 mg BID, about 150 mg BID, about 200 mg BID, about 250 mg BID, about 300 mg BID, about 350 mg BID, about 400 mg BID, about 450 mg BID, about 500 mg BID, about 550 mg BID, about 600 mg BID, about 650 mg BID, about 700 mg BID, about 800 mg BID, about 900 mg BID, about 1100 mg BID, about 1200 mg BID, about 1300 mg BID, about 1400 mg BID, about 1500 mg BID, or about 1600 mg BID, about 1700 mg BID, or about 1800 mg BID. In other embodiments, the compound of formula I, or a pharmaceutically acceptable salt thereof, or a pharmaceutical composition thereof, is administered orally at a unit dosage of about 200 mg BID, about 600 mg BID, or about 800 mg BID, or about 900 mg BID, or about 1200 mg BID. In some embodiments, the compound of formula I, or a pharmaceutically acceptable salt thereof, or a pharmaceutical composition thereof, is administered orally at a unit dosage of about 200 mg BID, or about 800 mg BID. In one embodiment, the compound of formula I, or a pharmaceutically acceptable salt thereof, or a pharmaceutical composition thereof, is administered orally at a unit dosage of about 800 mg BID.

Articles of Manufacture and Kits

Compositions (including, for example, formulations and unit dosages) comprising the compound of formula I, or a pharmaceutically acceptable salt thereof, can be prepared and placed in an appropriate container, and labeled for treatment of an indicated condition. Accordingly, provided is also an article of manufacture, such as a container comprising a unit dosage form of the compound of formula I, or a pharmaceutically acceptable salt thereof, and a label containing instructions for use of the compounds. In some embodiments, the article of manufacture is a container comprising a unit dosage form of the compound of formula I, or a pharmaceutically acceptable salt thereof, and at least one pharmaceutically acceptable vehicle.

Kits also are contemplated. For example, a kit can comprise unit dosage forms of the compound of formula I, or a pharmaceutically acceptable salt thereof, and a package insert containing instructions for use of the composition in treatment of a medical condition. In some embodiments, the kits comprises a unit dosage form of the compound of formula I, or a pharmaceutically acceptable salt thereof, and at least one pharmaceutically acceptable vehicle.

The instructions for use in the kit may be for treating a cancer, including, for example, a hematologic malignancy. In some embodiments, the instructions for use in the kit may be for treating cancer, such as leukemia or lymphoma, including relapsed and refractory leukemia or lymphoma. In certain embodiments, the instructions for use in the kit may be for treating acute lymphocytic leukemia (ALL), acute myeloid leukemia (AML), chronic lymphocytic leukemia (CLL), small lymphocytic lymphoma (SLL), myelodysplastic syndrome (MDS), myeloproliferative disease (MPD), chronic myeloid leukemia (CML), multiple myeloma (MM), non-Hodgkin's lymphoma (NHL), indolent non-Hodgkin's lymphoma (iNHL), refractory iNHL, mantle cell lymphoma (MCL), follicular lymphoma (FL), Waldestrom's macroglobulinemia (WM), T-cell lymphoma, B-cell lymphoma, diffuse large B-cell lymphoma (DLBCL), lymphoplasmacytic lymphoma (LPL), or marginal zone lymphoma (MZL). In one embodiment, the instructions for use in the kit may be for treating chronic lymphocytic leukemia (CLL) or non-Hodgkin's lymphoma (NHL). In one embodiment, the NHL is diffuse large B-cell lymphoma (DLBCL), mantle cell lymphoma (MCL), follicular lymphoma (FL), small lymphocytic lymphoma (SLL), lymphoplasmacytic lymphoma (LPL), and marginal zone lymphoma (MZL). In one embodiment, the hematologic malignancy is indolent non-Hodgkin's lymphoma (iNHL). In certain embodiments, diseases or conditions indicated on the label can include, for example, treatment of cancer.

In certain embodiments of the article of manufacture or the kit, the unit dosage has about 50 mg, about 100 mg, about 150 mg, about 200 mg, about 250 mg, about 300 mg, about 350 mg, about 400 mg, about 450 mg, about 500 mg, about 550 mg, about 600 mg, about 650 mg, about 700 mg, about 800 mg, about 900 mg, about 1100 mg, about 1200 mg, about 1300 mg, about 1400 mg, about 1500 mg, or about 1600 mg, about 1700 mg, or about 1800 mg of the compound of formula I, or a pharmaceutically acceptable salt thereof. In one embodiment, the unit dosage has about 800 mg of the compound of formula I, or a pharmaceutically acceptable salt thereof. In one embodiment of the article of manufacture or the kit, the unit dosage of the compound of formula I, or a pharmaceutically acceptable salt thereof, is a tablet.

Also provided is the use of a compound of formula I:

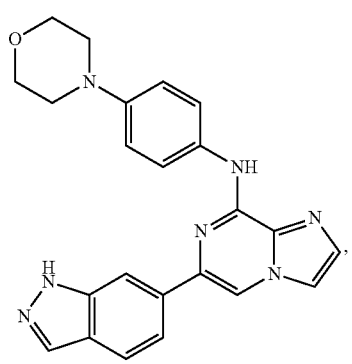

(I)

or a pharmaceutically acceptable salt thereof, in the manufacture of a medicament for the treatment of cancer in a human, wherein the human has a 17p deletion, a TP53 mutation, a NOTCH1 mutation, a SF3B1 mutation, a 11q deletion, or any combination thereof. One embodiment provides for the use of a compound of formula I, or a pharmaceutically acceptable salt thereof, in the manufacture of a medicament for the treatment of chronic lymphocytic leukemia in a human, wherein the human has a 17p deletion, a TP53 mutation, a NOTCH1 mutation, a SF3B1 mutation, a 11q deletion, or any combination thereof. Another embodiment provides for the use of a compound of formula I, or a pharmaceutically acceptable salt thereof, in the manufacture of a medicament for the treatment of non-Hodgkin's lymphoma in a human, wherein the human has a 17p deletion, a TP53 mutation, a NOTCH1 mutation, a SF3B1 mutation, a 11q deletion, or any combination thereof. Still another embodiment provides for the use of a compound of formula I, or a pharmaceutically acceptable salt thereof, in the manufacture of a medicament for the treatment of a cancer in a human, wherein the human has a 17p deletion, a TP53 mutation, a NOTCH1 mutation, a SF3B1 mutation, a 11q deletion, or any combination thereof, and wherein the cancer is selected from the group of acute lymphocytic leukemia (ALL), acute myeloid leukemia (AML), chronic lymphocytic leukemia (CLL), small lymphocytic lymphoma (SLL), and myelodysplastic syndrome (MDS).

Also provided is the use of a compound of formula I, or a pharmaceutically acceptable salt thereof, in the treatment of cancer in a human, wherein the human has a 17p deletion, a TP53 mutation, a NOTCH1 mutation, a SF3B1 mutation, a 11q deletion, or any combination thereof. One embodiment provides the use of a compound of formula I, or a pharmaceutically acceptable salt thereof, in the treatment of chronic lymphocytic leukemia in a human, wherein the human has a 17p deletion, a TP53 mutation, a NOTCH1 mutation, a SF3B1 mutation, a 11q deletion, or any combination thereof. Another embodiment provides the use of a compound of formula I, or a pharmaceutically acceptable salt thereof, in the treatment of non-Hodgkin's lymphoma in a human, wherein the human has a 17p deletion, a TP53 mutation, a NOTCH1 mutation, a SF3B1 mutation, a 11q deletion, or any combination thereof. Still another embodiment provides the use of a compound of formula I, or a pharmaceutically acceptable salt thereof, in the treatment of a cancer in a human, wherein the human has a 17p deletion, a TP53 mutation, a NOTCH1 mutation, a SF3B1 mutation, a 11q deletion, or any combination thereof, and wherein the cancer is selected from the group of acute lymphocytic leukemia (ALL), acute myeloid leukemia (AML), chronic lymphocytic leukemia (CLL), small lymphocytic lymphoma (SLL), and myelodysplastic syndrome (MDS), myeloproliferative disease (MPD), chronic myeloid leukemia (CML), multiple myeloma (MM), non-Hodgkin's lymphoma (NHL), indolent non-Hodgkin's lymphoma (iNHL), refractory iNHL, mantle cell lymphoma (MCL), follicular lymphoma (FL), Waldestrom's macroglobulinemia (WM), T-cell lymphoma, B-cell lymphoma, diffuse large B-cell lymphoma (DLBCL), lymphoplasmacytic lymphoma (LPL), and marginal zone lymphoma (MZL).

EXAMPLES

The following examples are included to illustrate embodiments of the disclosure, and are not intended to limit the scope of the disclosure. It should be appreciated by those of skill in the art that the techniques disclosed herein represent techniques that apply in the practice of the disclosure. Those of skill in the art would appreciate, in light of the present disclosure, that changes can be made in the examples herein without departing from the spirit and scope of the disclosure.

Example 1

Effect of the Compound of Formula I in Chronic Lymphocytic Leukemia (CLL) and Non-Hodgkin Lymphoma (NHL) Subjects This Example evaluates the efficacy of the compound of formula I, or a pharmaceutically acceptable salt thereof, in human subjects who have a hematologic malignancy, such as CLL or NHL, and are refractory to at least one chemotherapy treatment, or are in relapse after treatment with chemotherapy for such hematologic malignancy. This Example also evaluates the safety and tolerability of the compound of formula I, or a pharmaceutically acceptable salt thereof, in such subjects, as well as the drug levels and pharmacodynamic measures of the compound of formula I, or a pharmaceutically acceptable salt thereof.

Figure 2:
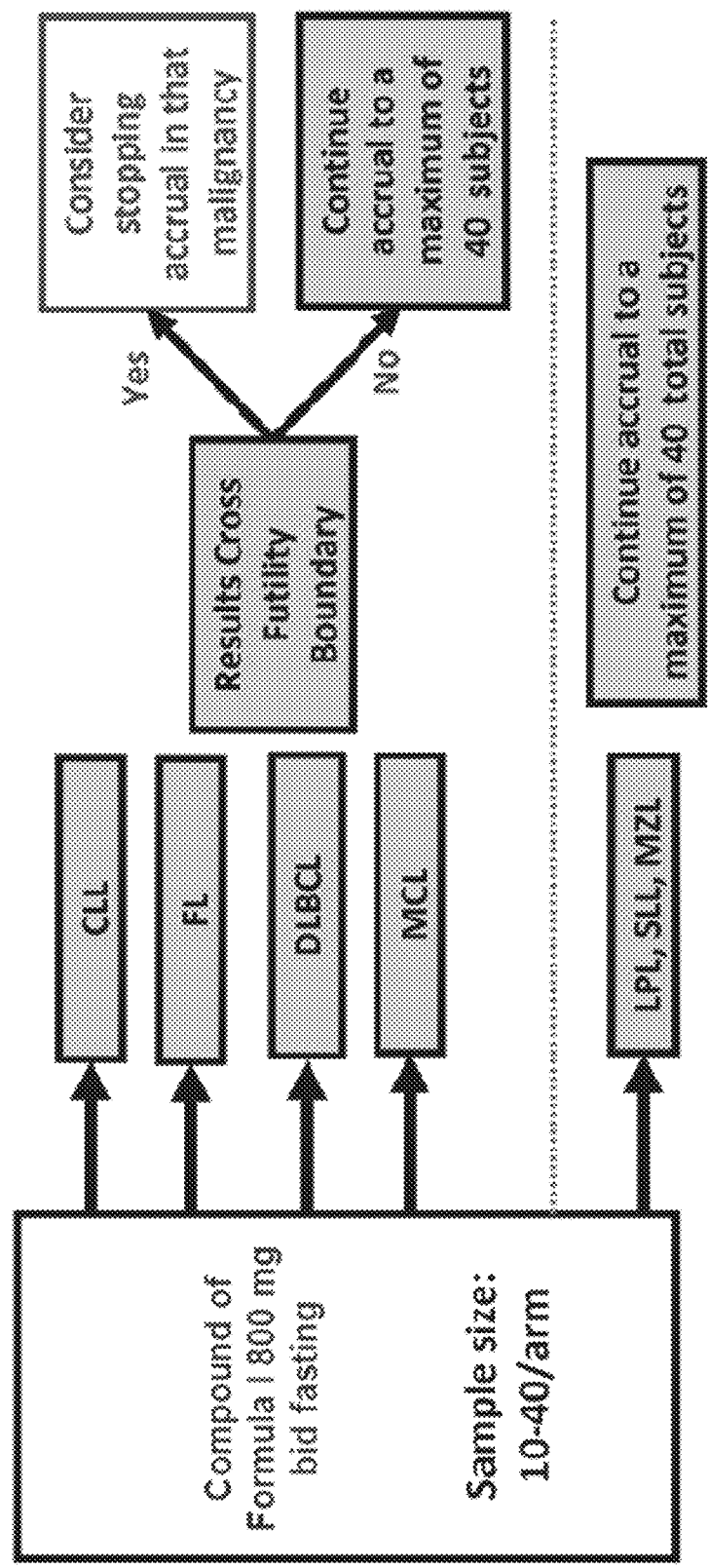
FIG. 2 is a process flow diagram depicting the trial of the compound of formula I, or a pharmaceutically acceptable salt thereof, in human subjects who suffer from certain hematologic malignancies.
Figure 3:
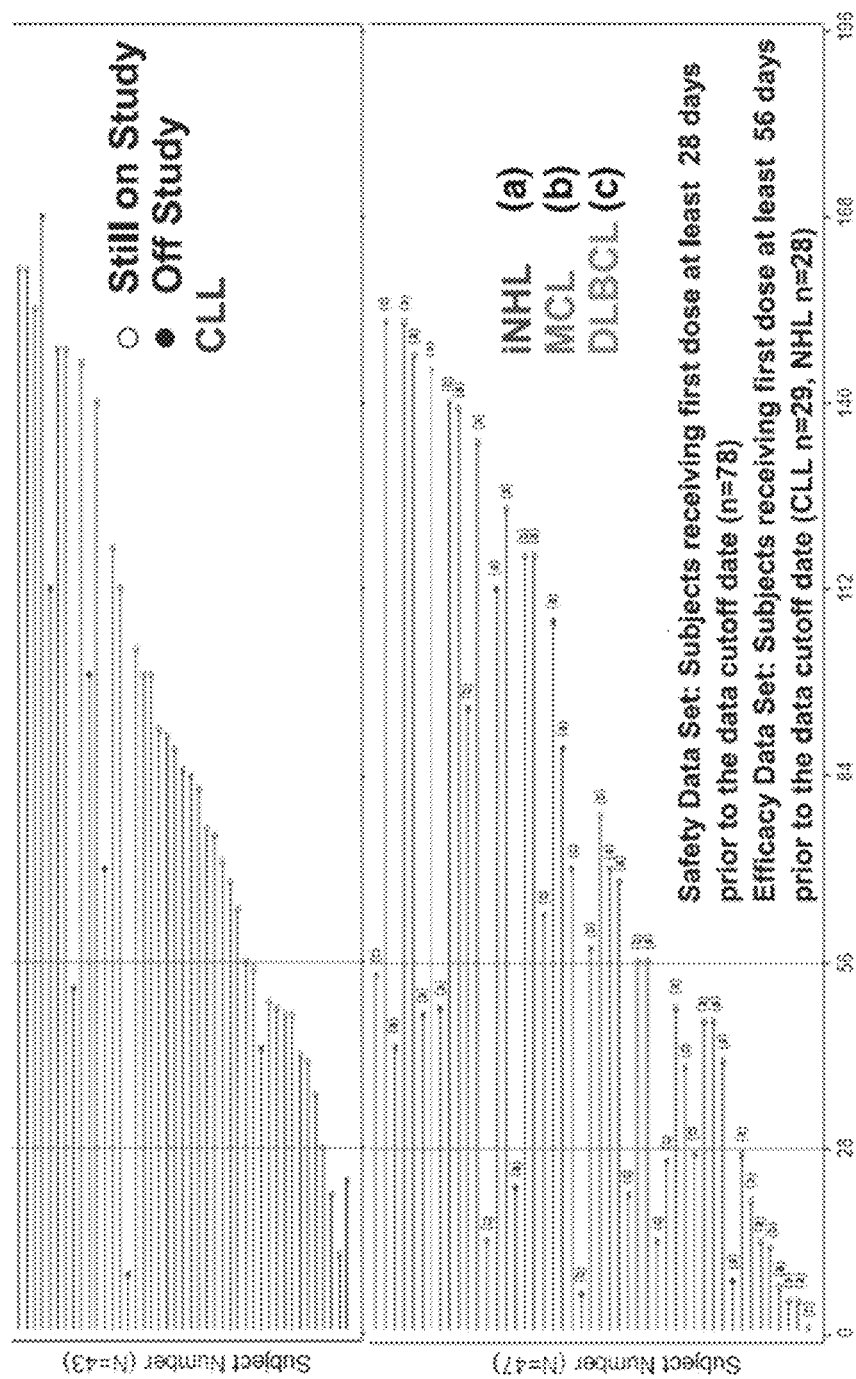
FIG. 3 is a graph depicting the subject time on study.

This Example was performed according to the process described in FIG. 2. The compound of formula I, or a pharmaceutically acceptable salt thereof, was administered to human subjects at a dose of 800 mg BID fasting. Subjects having various hematologic malignancies were evaluated, including subjects with chronic lymphocytic leukemia (CLL), follicular lymphoma (FL), diffuse large B-cell lymphoma (DLBCL), mantle cell lymphoma (MCL), lymphoplasmacytic lymphoma (LPL), small lymphocytic lymphoma (SLL), and marginal zone lymphoma (MZL). The sample size was 10-40/arm.

Subject Time on Study

A first set of data was collected to determine safety in subjects receiving a first dose of the compound of formula I, or a pharmaceutically acceptable salt thereof, at least 28 days prior to the data cutoff date (n=78). A second set of data was collected to determine efficacy in subjects receiving a first dose of the compound of formula I, or a pharmaceutically acceptable salt thereof, at least 56 days prior to the data cutoff date (CLL n=29; NHL n=28).

The subject characteristics (for the safety data set) are summarized in Table 1 below.

TABLE 1

|  | CLL N = 39 | NHL N = 39 | ALL N = 78 |
| --- | --- | --- | --- |
| Gender, Male | 29 (74.4%) | 23 (59.0%) | 52 (66.7%) |
| Age, median [range], years | 73 [51, 89] | 71 [47, 89] | 72 [47, 89] |
| Median # of Prior therapies [Range] | 2 [1, 6] | 3 [1, 8] | 2 [1, 8] |
| Anti-CD20 Antibody | 38 (97.4%) | 38 (97.4%) | 76 (97.4%) |
| Any Alkylating agent | 33 (84.6%) | 37 (94.9%) | 70 (89.7%) |
| Bendamustine | 23 (59.0%) | 17 (43.6%) | 40 (51.3%) |
| Any Purine Analog | 25 (64.1%) | 10 (25.6%) | 35 (44.9%) |
| Fludarabine | 25 (64.1%) | 9 (23.1%) | 34 (43.6%) |
| Anthracyclines | 3 (7.7%) | 25 (64.1%) | 28 (35.9%) |

The disposition and exposure for the safety data set is summarized in Table 2 below.

TABLE 2

|  | CLL N = 39 | NHL N = 39 | ALL N = 78 |
| --- | --- | --- | --- |
| Continuing Study Drug | 32 (82.1%) | 18 (46.2%) | 50 (64.1%) |
| Exposure (weeks), median [range] | 12 [1, 24] | 8 [1, 22] | 10 [1, 24] |
| Reasoning for discontinuing Study Drug |  |  |  |
| Adverse Events | 3 (7.7%) | 8 (20.5%) | 11 (14.1%) |
| Related AEs | 2 (5.1%) | 4 (10.3%) | 6 (7.7%) |
| Progressive Disease | 4 (10.3%) | 11 (28.2%) | 15 (19.2%) |
| Investigator's Discretion | 0 | 1 (2.6%) | 1 (1.3%) |
| Withdrawn Consent | 0 | 1 (2.6%) | 1 (1.3%) |

Investigator Assessed Nodal Responses

Figure 4:
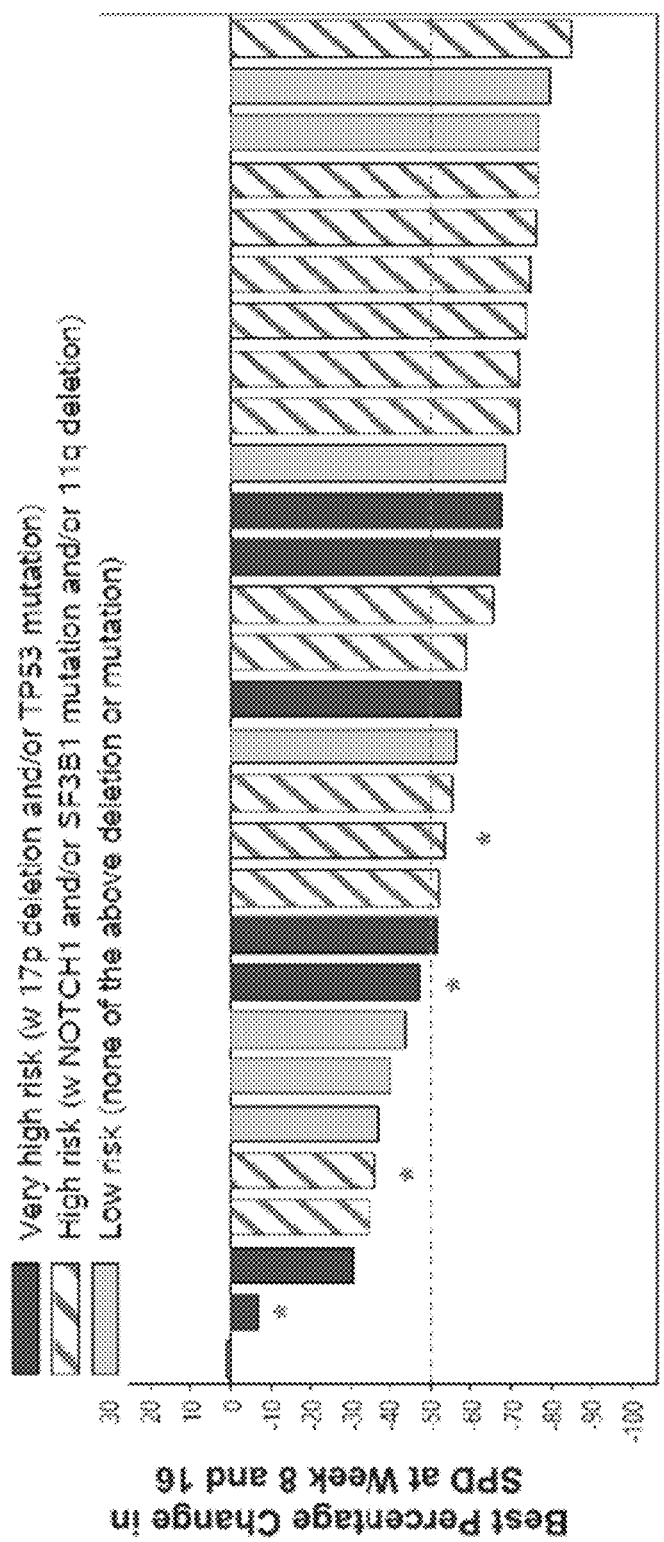
FIG. 4 is a graph depicting the investigator assessed nodal response of the compound of formula I, or a pharmaceutically acceptable salt thereof, in human subjects with CLL (Efficacy Date Set, n=29).

The efficacy of the compound of formula I, or a pharmaceutically acceptable salt thereof, in CLL subjects (n=29) and NHL subjects (n=24) were also examined based on nodal responses rates. FIG. 4 summarizes the effect on (i) very high risk, (ii) high risk, and (iii) low risk CLL subjects. 'Very high risk' CLL subjects in this Example had 17p deletion and/or TP53 mutation. 'High risk' CLL subjects had a NOTCH1 mutation and/or SF3B1 mutation and/or 11q deletion. 'Low risk' CLL subjects had none of the deletions or mutations described above. The overall nodal response rate in CLL subjects was observed to be 69%.

Figure 5:
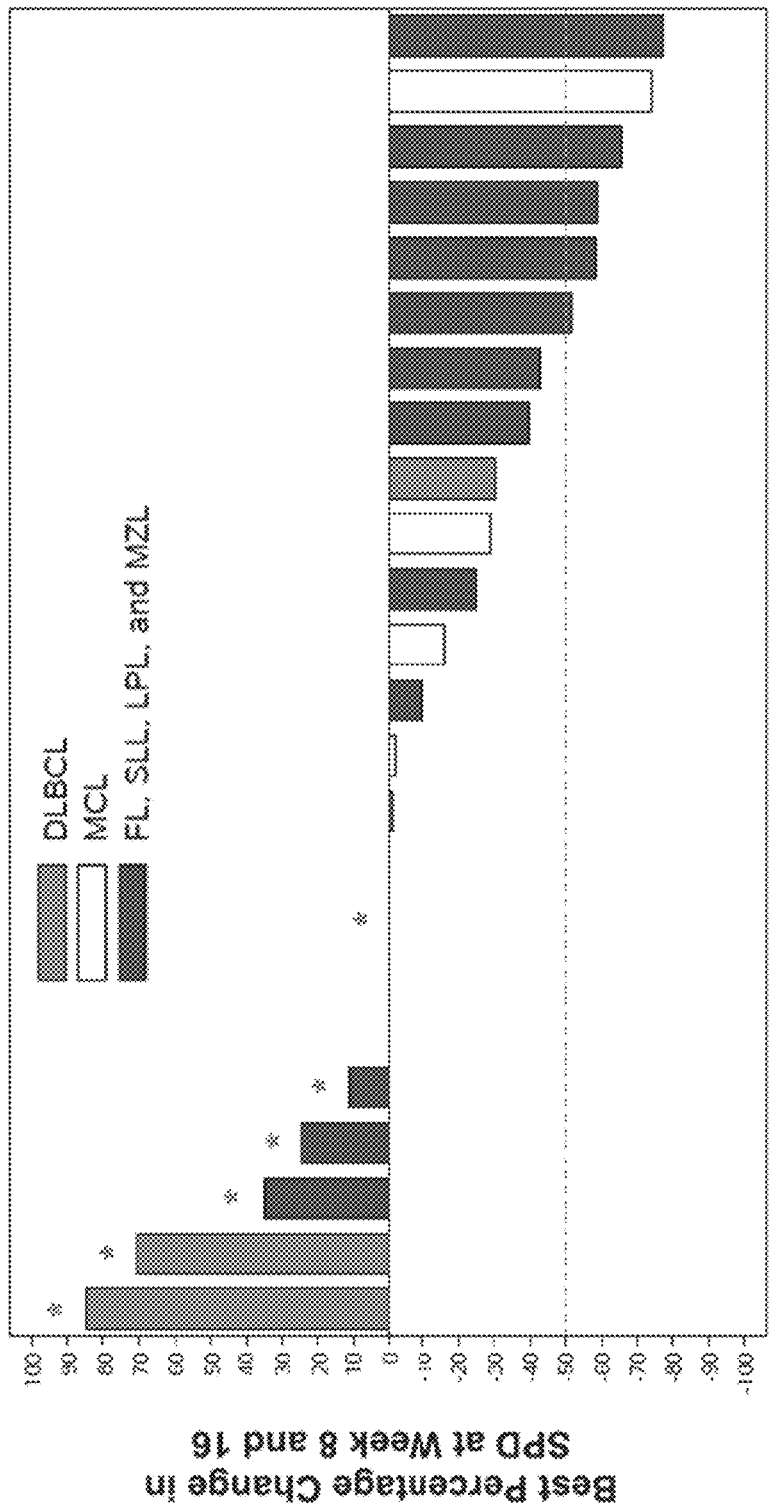
FIG. 5 is a graph depicting the investigator assessed nodal response of the compound of formula I, or a pharmaceutically acceptable salt thereof, in human subjects with NHL (Efficacy Date Set, n=24).

FIG. 5 summarizes the effect on subjects with (i) DLBCL, (ii) MCL, or (iii) FL, SLL, LPL and MZL.

Figure 6:
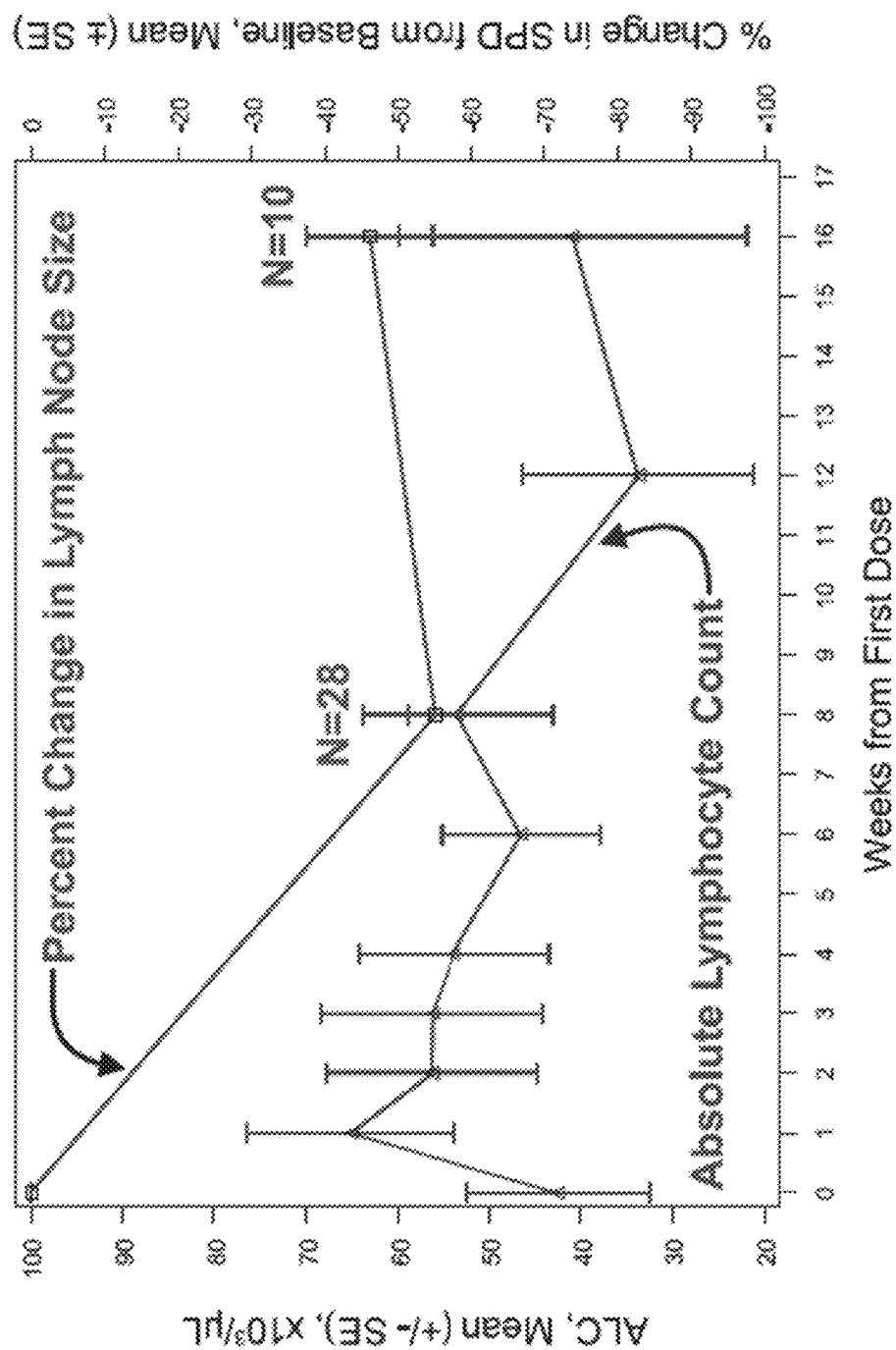
FIG. 6 is a graph depicting the relationship between absolute lymphocyte count (ALC) and tumor burden over time in human subjects with CLL.

Relationship Between Absolute Lymphocyte Count (ALC) and Tumor Burden Over Time in CLL Subjects The effect of the compound of formula I, or a pharmaceutically acceptable salt thereof, was examined in CLL subjects over 17 weeks from the first dose, comparing absolute lymphocyte count (ALC) and the change in lymph node side. FIG. 6 summarizes the results of such study.

Safety

The safety of the compound of formula I, or a pharmaceutically acceptable salt thereof, administered to the human subjects was also monitored. Table 3 below summarizes the treatment-emergent non-hematologic adverse events. Such adverse events were observed in ≥10% of the subjects (Safety Data Set, N=78).

TABLE 3

|  | Grade 1 | Grade 2 | Grade 3 | Grade 4 | All Grades |
| --- | --- | --- | --- | --- | --- |
| Any event |  |  |  |  | 73 (93.6) |
| Fatigue | 13 | 16 | 5 |  | 34 (43.6) |
| Nausea | 18 | 4 | 2 |  | 24 (30.8) |
| Diarrhea | 20 | 2 |  |  | 22 (28.2) |
| Constipation | 11 | 5 | 1 |  | 17 (21.8) |
| Decreased appetite | 10 | 6 |  |  | 16 (20.5) |
| Headache | 13 | 2 | 1 |  | 16 (20.5) |
| Pyrexia | 9 | 6 |  |  | 15 (19.2) |
| Dizziness | 14 |  |  |  | 14 (17.9) |
| Cough | 9 | 1 | 1 |  | 11 (14.1) |
| Insomnia | 8 | 3 |  |  | 11 (14.1) |
| Oedema peripheral | 8 | 2 |  |  | 10 (12.8) |
| Dyspepsia | 3 | 5 |  |  | 8 (10.3) |
| Vomiting | 6 | 2 |  |  | 8 (10.3) |

Figure 7:
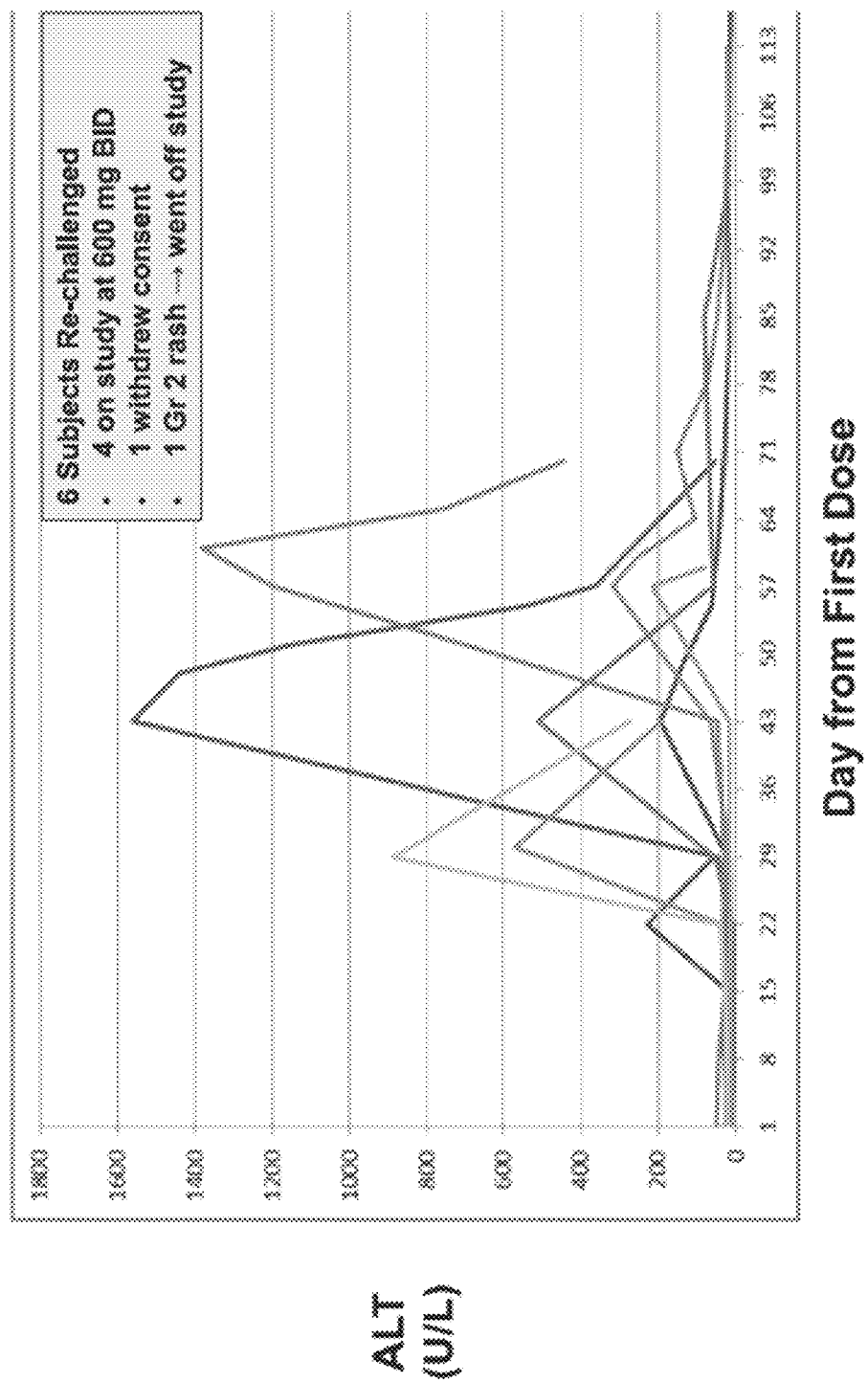
FIG. 7 is a graph depicting the Grade 3 and 4 reversible ALT elevations that occurred in 9 of 78 human subjects (12%).

Alanine aminotransferase (ALT) was also measured in the subjects. FIG. 7 shows the results of this study; Grade 3 and 4 reversible ALT elevations was observed to occur in 9 out of 78 subjects (12%).

Effects on BCR-Mediated Signaling Pathways

Figure 8:
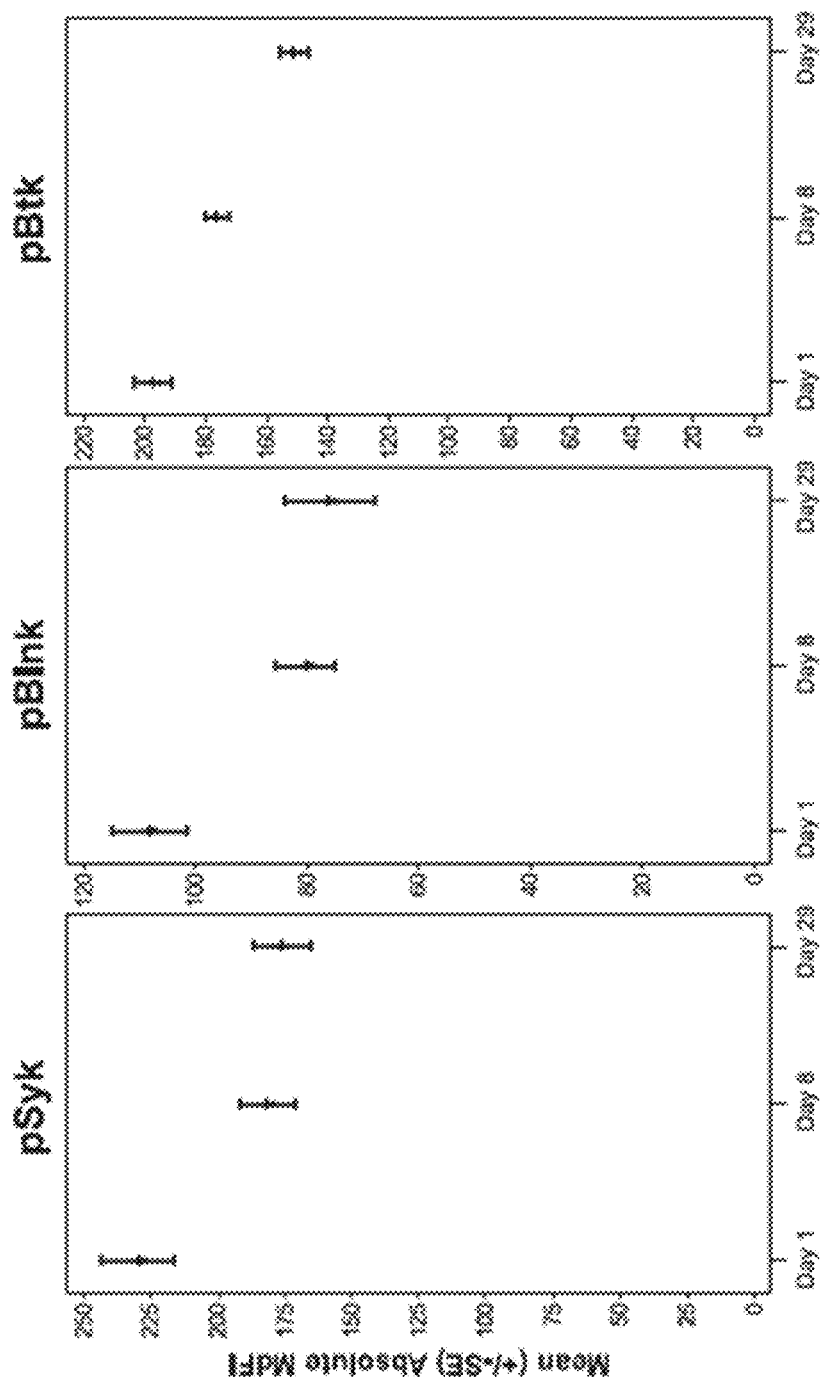
FIG. 8 provides a set of graphs depicting the pathway modulation following administration of the compound of formula I, or a pharmaceutically acceptable salt thereof, in human subjects with CLL (n=35).

The effects of the compound of formula I, or a pharmaceutically acceptable salt thereof, on B-Cell Receptor (BCR)-mediated signaling in peripheral blood mononucleated cell (PBMC) was measured in blood samples collected from human subjects prior to (Day 1) and after treatment (Days 8 and 29). As seen in FIG. 8, downregulation of phosphorylated Syk, Blnk and Btk in CD19+CD5+ circulating tumor cells was detected using intracellular phosphoprotein flow cytometry. Nominal p-values from tests of mean change of Day 8 and 29 from Day 1 using mixed model for repeated measures are <0.0005.

Figure 9:
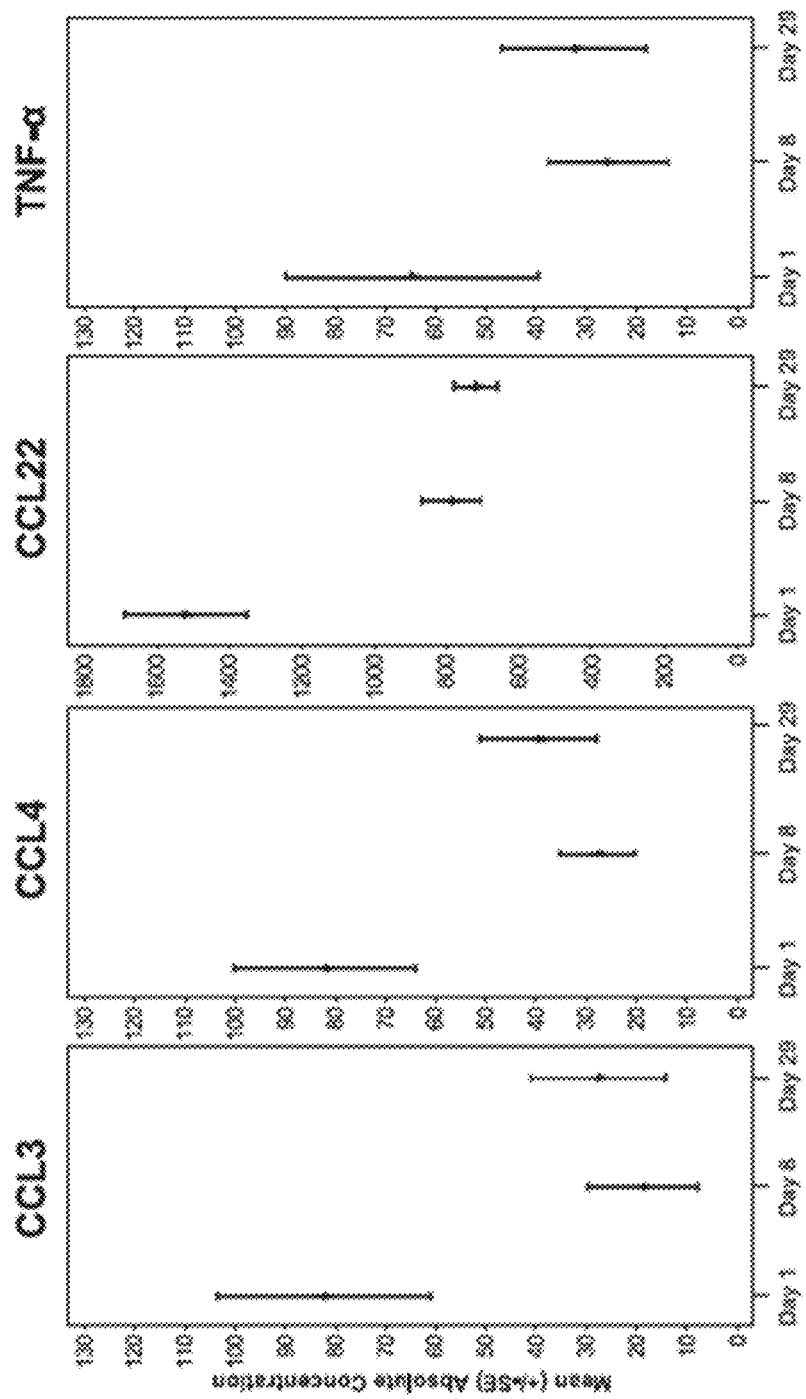
FIG. 9 provides a set of graphs depicting the inhibition of BCR-mediated chemokine/cytokines after administration with the compound of formula I, or a pharmaceutically acceptable salt thereof, in human subjects with CLL (n=20).

Plasma levels of CCL3/MIP1alpha, CCL4/MIP1beta, CCL22/MDC, and TNFalpha were measured on Day 1 prior to treatment with the compound of formula I, or a pharmaceutically acceptable salt thereof, and on Days 8 and 29 by Luminex immunoassays. FIG. 9 summarizes the inhibition of BCR-mediated chemokine/cytokines after treatment in CLL subjects. Nominal p-values from tests of mean change of Day 8 and 29 from Day 1 using mixed model for repeated measures are <0.0001.

Example 2

The safety and efficacy of entospletinib was tested in a phase 2 trial in separate cohorts of subjects with CLL, indolent non-Hodgkin lymphoma (iNHL), mantle cell lymphoma (MCL), or diffuse large B-cell lymphoma (DLBCL). This trial was registered at www.clinicaltrials.gov as #NCT01799889.

Methods

Study Design and Conduct

A phase 2, open-label, single-agent study was completed to evaluate the efficacy, safety, tolerability, and pharmacodynamics of entospletinib in subjects with relapsed or refractory hematologic malignancies. Five separate cohorts consisting of subjects with CLL, follicular lymphoma (FL), other iNHLs (including lymphoplasmacytoid lymphoma, small lymphocytic lymphoma [SLL], and marginal zone lymphoma), MCL, or DLBCL were enrolled. A Bayesian, continuous data review approach was used to update the estimates of progression-free survival (PFS) rates at 16 weeks (MCL and DLBCL) or 24 weeks (CLL and FL) and to assess futility with a maximum of 40 subjects per cohort.

Eligibility

Subjects who were at least 18 years of age with a documented diagnosis of CLL, as established by the International Workshop on CLL, with progressive disease (PD) were eligible for the study. Prior treatment for CLL must have comprised either (1) a regimen containing a therapeutic antibody administered for two or more doses of antibody treatment or (2) a regimen containing at least one cytotoxic agent administered for two or more cycles of cytotoxic treatment. The presence of radiographically measurable lymphadenopathy or extranodal lymphoid malignancy as assessed by computed tomography (CT) or magnetic resonance imaging (MRI) was required for enrollment. All acute toxic effects of prior antitumor therapy must have resolved to grade 1 or lower before the start of the study drug, with the exception of alopecia (grade 1 or 2 permitted), neurotoxicity (grade 1 or 2 permitted), or bone marrow parameters (grade 1, 2, or 3 permitted). A Karnofsky performance status of at least 60% and a life expectancy of at least 3 months were required. Required screening laboratory data were collected within 5 weeks before administration of study drug. Subjects with any degree of neutropenia, thrombocytopenia, or anemia attributed to the malignancy by the treating physician were eligible to enroll.

Subjects were not eligible if they met any of the following criteria: known active central nervous system lymphoma; intermediate- or high-grade myelodysplastic syndrome, history of a nonlymphoid malignancy with limited exceptions, evidence of an ongoing systemic infection, pregnant or breastfeeding, history or prior allogeneic bone marrow progenitor cell or solid organ transplantation, or receipt of investigational medication within 21 days of study entry. Current therapy with agents that reduce gastric acidity was not allowed.

Treatment

Treatment with entospletinib was at a dose of 800 mg twice a day over 28-day cycles under fasted conditions. Fasting was defined as no food or liquids other than water for 2 hours pre- and 1 hour post-dose.

Assessments

Clinic visits, including laboratory tests and pharmacodynamic measurements, were scheduled for day 1 of each 28-day cycle. Blood samples for pharmacokinetic analyses of entospletinib were collected on day 1 of each 28-day cycle, on days 8, 15, and 22 of cycle 1 and on day 15 of cycle 2. Additional safety monitoring visits took place on days 8, 15, and 22 of cycle 1 and day 15 of cycle 2.

Procedures to assess tumor response were conducted every 8 weeks during the first 24 weeks on study and then every 12 weeks thereafter until disease progression or the start of other antitumor therapies, regardless of cycle number or dose interruptions. CT or MRI scans were used to document sites of disease, identify target lesions, and assess response and disease progression. Determination of response and progression was based on standardized International Workshop on CLL criteria as modified by Cheson et al. (*J Clin Oncol.* 2012; 30(23):2820-2822). The findings of an independent review committee were used for analyses of PFS and other tumor control end points.

A bone marrow biopsy and aspirate were collected for confirmatory purposes for all subjects who achieved a complete response (CR) or to confirm suspected PD based solely upon declines in the platelet count and/or hemoglobin. Pharmacodynamic assessments, including serum cytokines and protein phosphorylation in circulating CLL cells, occurred before starting therapy and at designated time points thereafter.

End Points

The primary end point was PFS rate at 24 weeks for subjects with CLL. Secondary end points included tolerability, objective response rate (ORR), duration of response (DOR), time to response, and lymph node response rate. Safety assessments, including all abnormal laboratory data and AEs, were performed by grading the laboratory values and AEs according to the Common Terminology Criteria for AEs version 4.03 (http://www.hrc.govt.nz/sites/default/files/CTCAE %20manual %20-%20DMCC.pdf). Exploratory end points included plasma drug concentrations and pharmacodynamic biomarkers.

Statistical Analyses

A Bayesian, continuous data review approach was used to update the estimates of PFS rates at 16 weeks (MCL and DLBCL) or 24 weeks (CLL and FL) and to assess futility with a maximum size of 40 subjects per cohort. The cohort was considered to have crossed the futility boundary if it was highly likely (>90%) that the PFS rate was less than 0.2 given the available efficacy outcomes data at 16 or 24 weeks.

PFS was defined as the interval from start of treatment to disease progression or death from any cause and analyzed using Kaplan-Meier methods. The findings of the Independent Review Committee (IRC) were considered primary for analyses of PFS and other tumor control responses. The ORR was defined as the proportion of subjects who had a CR or partial response (PR). DOR was defined as the time from when the first response (CR or PR) was achieved until the earlier of the first documentation of definitive disease progression or death from any cause. The lymph node response rate was defined as the proportion of subjects who had a decrease of 50% or more in lymphadenopathy, irrespective of lymphocyte count.

Results

Subjects

Forty-one subjects with CLL were enrolled in the and were included for the efficacy analysis. One hundred and forty-five subjects with CLL or NHL were included for the safety analysis. For the 41 CLL subjects, the median age was 73 years (range 51-89 years), 68% were male, and the median number of prior treatment regimens was 2 (range 1-8). Prior treatments included anti-CD20 antibodies (97.6%), alkylating agents (85.4%; bendamustine [63.4%]); and fludarabine (68.3%). Ten subjects (24.4%) had very high risk features (17p deletions/TP53 mutations), and additional 17 subjects (41.5%) had high risk features (NOTCH1 or SF3B1 mutation, or 11q deletion). The most common reasons for discontinuation of study drug were progressive disease and AEs (Table 4).

TABLE 4

Characteristics of the subjects with CLL at baseline and study status (N = 41)

| | | |
|---|---|---|
| Median age (range), year | 73 (51-89) | |
| Rai Stage (% of subjects) | | |
| 0 | 3 (7.3%) | |
| 1 or 2 | 19 (46.3%) | |
| 3 or 4 | 19 (46.3%) | |
| Extent of CLL (% of subjects) | | |
| Anemia | | |
| Any grade | 21 (51.2%) | |
| Grade ≥3 | 0 | |
| Neutropenia | | |
| Any grade | 14 (34.1%) | |
| Grade ≥3 | 2 (4.9%) | |
| Thrombocytopenia | | |
| Any grade | 22 (53.7%) | |
| Grade ≥3 | 1 (2.4%) | |
| Median absolute lymphocyte count (range), mm$^3$ | 30,070 (740-222,200) | |
| Median estimated creatinine clearance (range), mL/min | 63.8 (25.2-123.6) | |
| Genetic risk factors (% of subjects) | | |
| Very high risk (17p deletion or TP53 mutation) | 10 (24.4%) | |
| High risk (NOTCH1 or SF3B1 mutation or 11q deletion) | 17 (41.5%) | |
| Low risk (none of the above mutations or deletions) | 12 (29.3%) | |
| Undetermined | 2 (4.9%) | |
| Unmutated IGHV | 31 (75.6%) | |
| Previous CLL treatment | | |
| Median no. of regimens (range) | 2 (1-8) | |
| Drugs (% of subjects) | | |
| Anti-CD20 Agents | 40 (97.6%) | |
| Rituximab | 39 (95.1%) | |
| Ofatumumab | 5 (12.2%) | |
| Alkylating agents | 35 (85.4%) | |
| Bendamustine | 26 (63.4%) | |
| Fludarabine | 28 (68.3%) | |
| Study status (%) | | 41 |
| Treated | 19 (46.3%) | 22 |
| Continued study drug | (53.7%) | 4 |
| Discontinued study drug | (8.8%) | 14 |
| AEs | (34.1%) | 1 |
| Progressive disease | (2.4%) | 2 |
| Death | (4.8%) | 1 (2.4%) |
| Investigator's decision | 22 (53.7%) | |
| Withdrawn consent | | |
| Discontinued study | | |

IGHV indicates immunoglobulin heavy chain variable.

Receipt of Study Drug

At the time of this analysis, the median time that CLL subjects had received entospletinib was 32 weeks (interquartile range [IQ], 15-42; simple range, 1-53), and 22 subjects (53.7%) received entospletinib for 6 months or longer. Eight subjects (19.5%) required at least one dose reduction from the starting dose, six subjects (14.6%) had their dose reduced to 600 mg, and two subjects (4.9%) had the dose reduced to 400 mg.

Efficacy

PFS.

The CLL cohort enrolled 41 subjects without crossing the futility boundary with a median follow up of 5.5 months. The primary end point of 24 weeks PFS was 69.8% (95% CI: 50.9%, 82.6%). Median PFS had not yet been reached (95% CI: 7.7 months, not reached). Seventy-five percent of the subjects have PFS longer than 5.4 months (95% CI: 3.5, 8.3). There were 13 subjects (31.7%) with events, 12 (29.3%) with disease progression, and one death (2.4%).

ORR in CLL Subjects.

The ORR was 56.1% (95% CI: 39.7%, 71.5%), with 23 subjects achieving a PR and no subject achieving a CR. Eighteen subjects (44%) had stable disease. Among the subjects with stable disease, two (4.9%) achieved nodal response (50% reduction in sum of the products of the diameters [SPD]) with persistent lymphocytosis. One (2.4%) had progressive disease, and 2 subjects (5%) did not have a post-baseline assessment (one died, and one withdrew consent prior to evaluation). There were no significant differences in ORR within subgroups, including sex, age, and number of prior therapies, IGHV mutation status, or 17p deletion/TP53 mutation status although a statistically insignificant trend toward lower response rate was seen in the 17P deletion/TP53 mutation. Fifteen of 23 responding subjects (65.2%) had a PR at the first post-baseline evaluation (scheduled at week 8).

DOR in CLL Subjects.

Among the 23 responding subjects, median DOR has not yet been reached (95% CI: 5.8 months, not reached). Seventy-five percent of subjects have DOR longer than 6.5 months (95% CI: 3.4 months, not reached).

Lymph Node Response in Subjects With CLL.

Of 39 evaluable subjects who had at least one post-baseline assessment, 94.5% achieved reduction in adenopathy: 61.5% (95% CI: 44.6%, 76.6%) of subjects achieved at least a 50% decrease in SPD from baseline, and 33% had a less than 50% decrease in SPD from baseline.

The mean absolute lymphocyte count in subjects rose from 50,090 to 72,980 lymphocytes per microliter on day 8 and then declined, returning to baseline by approximately 3 months and then declining further.

Safety

The safety analysis includes all treated subjects (N=145) in each cohort of the study, including those with CLL, FL, lymphoplasmacytoid lymphoma/SLL/marginal zone lymphoma, MCL, or DLBCL. Of all treated subjects, 94.5% had at least one AE. Treatment-emergent, nonhematologic AEs occurring in 15% or higher in any grade of all subjects, serious AEs occurring in at least 2%, and common laboratory abnormalities are reported in Table 2. The most common AEs were fatigue and gastrointestinal disturbances. Most AEs were grade 2 or lower.

Grade 3 fatigue was reported in 10 subjects (6.9%), grade 3 nausea was reported in five subjects (3.4%), and grade 3 dyspnea was reported in nine subjects (6.2%). One subject (0.7%) experienced grade 4 rash, two subjects (1.4%) had grade 3 rash, and two subjects (1.4%) had grade 2 rash.

Forty-five subjects (31.0%) experienced a treatment-emergent, serious AE, the most common of which included dyspnea (n=5), pneumonia (n=5), febrile neutropenia (n=4), and pyrexia (n=4). Twenty-two subjects (15.2%) experienced a treatment-emergent AE that led to study drug discontinuation, including increased alanine aminotransferase (ALT; n=3), fatigue (n=3), and headache (n=3).

Common laboratory abnormalities reported for any subjects enrolled in the trial are listed in Table 5. Subjects were allowed to enroll in the study if they had cytopenias due to CLL. Treatment-emergent cytopenias were defined as a cytopenia that worsened in the period from the first dose of study treatment to 30 days after the last dose of study treatment. Grade 3 or higher neutropenia was reported in 21 subjects (14.5%), and grade 3 or higher anemia was reported in 11 subjects (7.6%). Reversible grade 3 or 4 ALT/AST elevations occurred in 21 of 145 subjects (14.5%), 10 of which occurred by 6 weeks (first and third quartile of 4.1 and 6.1 weeks, respectively; all but one event occurred by 10 weeks); 12 of 21 subjects (57.1%) resumed after interruption without further event; one remained on interruption; seven discontinued due to other reasons while entospletinib was being withheld; and one withdrew due to ALT/AST elevation.

TABLE 5

Treatment-emergent AEs and laboratory abnormalities (N = 145)

| | Any grade, n (%) | At least grade 3, n (%) |
|---|---|---|
| AE (at least 15% nonhematologic AEs in any grade) | | |
| Fatigue | 75 (51.7) | 10 (6.9) |
| Nausea | 58 (40) | 5 (3.4) |
| Diarrhea | 50 (34.5) | 1 (0.7) |
| Constipation | 35 (24.1) | 2 (1.4) |
| Decreased appetite | 35 (24.1) | 1 (0.7) |
| Headache | 33 (22.8) | 1 (0.7) |
| Pyrexia | 31 (21.4) | 3 (2.1) |
| Dizziness | 30 (20.7) | 1 (0.7) |
| Cough | 28 (19.3) | 1 (0.7) |
| Insomnia | 23 (15.9) | 0 |
| Serious AE (at least 2%) | | |
| Dyspnea | 5 (3.4) | |
| Pneumonia | 5 (3.4) | |
| Febrile neutropenia | 4 (2.8) | |
| Pyrexia | 4 (2.8) | |
| Anemia | 3 (2.1) | |
| Back pain | 3 (2.1) | |
| Chest pain | 3 (2.1) | |
| Dehydration | 3 (2.1) | |
| Laboratory abnormality | | |
| Neutropenia | 47 (32.4) | 21 (14.5) |
| Anemia | 54 (37.2) | 11 (7.6) |
| Thrombocytopenia | 10 (6.9) | 4 (2.8) |
| Total bilirubin | 45 (31.0) | 6 (4.1) |
| Increased ALT | 54 (37.2) | 20 (13.8) |
| Increased AST | 49 (33.8) | 18 (12.4) |

AST indicates aspartate aminotransferase.

Pharmacokinetics and Pharmacodynamics

The mean (% coefficient of variation) entospletinib plasma pharmacokinetic exposure parameters were as follows: $C_{max}$: 1490 (38%) ng/mL, $AUC_{tau}$: 15,500 (40%) ng/h/mL, and $C_{trough}$: 1100 (44%) ng/mL. Overall, the entospletinib $C_{trough}$ was well above the in vitro, whole blood, half maximal response concentration ($EC_{50}$) for Syk inhibition (314 ng/mL).

Significant reductions in the serum levels of BCR-induced CCL3 and CCL4 chemokines were observed in subjects at first evaluation on days 8 and 29 of treatment (nominal P<0.0001). Serum levels of CCL22 and tumor necrosis factor alpha (TNF-α) were also inhibited on days 8 and 29 of therapy (nominal P<0.0001).

Discussion

Shown is the preliminary efficacy of orally available entospletinib in subjects with relapsed and refractory CLL and safety in a larger cohort of patients with various histologies of NHL in addition to CLL. This multicenter, single-arm, phase 2 study, showed that entospletinib is well tolerated and demonstrates clinical activity in subjects with relapsed CLL.

With a median follow-up of 5.5 months, median PFS had not yet been reached; 69.8% of patients were alive and without disease progression at 24 weeks, the primary end point of this study. Entospletinib activity compares favorably to a population of CLL subjects with similar median age and prior therapies treated with rituximab monotherapy who had a 24-week PFS of 46% (Furman et al., *New Engl J Med.* 2014; 370(11):997-1007). In addition, this study saw an ORR of 56.1% with 2 additional subjects (4.9%) with a nodal response with persistent lymphocytosis, a clinical behavior observed with other agents that disrupt BCR signaling. Entospletinib was well tolerated with mild gastrointestinal AEs (nausea, diarrhea, constipation, dyspepsia) occurring most commonly and resulting in dose reduction or discontinuation in 7.6% and 14.5% of all treated subjects (N=145), respectively. Grade 3/4 reversible transaminase elevation occurred in 14.5% and grade 3/4 neutropenia at 14.5%. Eighteen (12.4%) subjects died while on study, 13 due to disease progression and five due to AEs, none attributed by the investigator to entospletinib. In the CLL cohort, three subjects died while on study (two of these subjects died after discontinuation of study drug); one due to sepsis and two due to progressive disease.

Entospletinib plasma pharmacokinetic parameters were consistent with previous data (Ramanathan S, Di Paolo J A, Doan T, Burge D. Single and multiple dose-ranging evaluation of safety, pharmacokinetics, and pharmacodynamics of GS-9973, a novel pSYK inhibitor. Poster presented at: American Association for Cancer Research; April 2013; Washington, D.C.), and the plasma exposures achieved corresponded to robust pharmacodynamics and efficacy. The reduction in circulating levels of CCL3 and CCL4 provide evidence of in vivo drug inhibition of BCR signaling in CLL. This is consistent with the proposed model in which Syk signaling facilitates retention of malignant lymphocytes within protective secondary lymphoid tissues.

What is claimed is:

1. A method for treating a hematologic malignancy in a human having a 17p deletion, a TP53 mutation, a NOTCH1 mutation, a SF3B1 mutation, a 11q deletion, or any combination thereof, comprising identifying a human in need of treatment for the hematologic malignancy and having one of said deletions or mutations, and administering to said human a therapeutically effective amount of a compound of formula I:

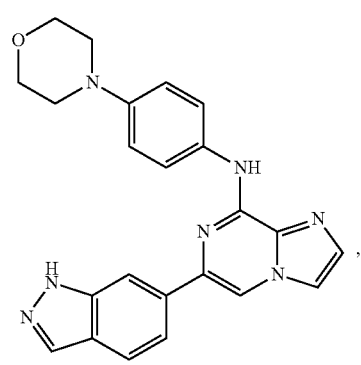

or a pharmaceutically acceptable salt thereof, wherein the compound of formula I or the pharmaceutically acceptable salt thereof is the only anti-cancer therapy administered to the human and wherein the hematologic malignancy is acute lymphocytic leukemia (ALL), acute myeloid leukemia (AML), chronic lymphocytic leukemia (CLL), small lymphocytic lymphoma (SLL), myelodysplastic syndrome (MDS), myeloproliferative disease (MPD), chronic myeloid leukemia (CML), multiple myeloma (MM), non-Hodgkin's lymphoma (NHL), indolent non-Hodgkin's lymphoma (iNHL), refractory iNHL, mantle cell lymphoma (MCL), follicular lymphoma (FL), Waldenstrom's macroglobulinemia (WM), T-cell lymphoma, B-cell lymphoma, diffuse large B-cell lymphoma (DLBCL), lymphoplasmacytic lymphoma (LPL), or marginal zone lymphoma (MZL).

2. The method of claim 1, wherein the human has a 17p deletion, a TP53 mutation, or a combination thereof.

3. The method of claim 1, wherein the human has a NOTCH1 mutation, a SF3B1 mutation, a 11q deletion, or any combination thereof.

4. The method of claim 1, wherein the human is refractory to at least one anti-cancer treatment.

5. The method of claim 1, wherein the human is in relapse after treatment with at least one anti-cancer treatment.

6. The method of claim 1, wherein the hematologic malignancy is acute lymphocytic leukemia (ALL).

7. The method of claim 1, wherein the hematologic malignancy is acute myeloid leukemia (AML).

8. The method of claim 1, wherein the hematologic malignancy is selected from the group consisting of chronic lymphocytic leukemia (CLL), small lymphocytic lymphoma (SLL), myelodysplastic syndrome (MDS), myeloproliferative disease (MPD), chronic myeloid leukemia (CML), multiple myeloma (MM), non-Hodgkin's lymphoma (NHL), indolent non-Hodgkin's lymphoma (iNHL), refractory iNHL, mantle cell lymphoma (MCL), follicular lymphoma (FL), Waldestrom's macroglobulinemia (WM), T-cell lymphoma, B-cell lymphoma, diffuse large B-cell lymphoma (DLBCL), lymphoplasmacytic lymphoma (LPL), and marginal zone lymphoma (MZL).

9. A method for treating a lymphoma in a human having a 17p deletion, a TP53 mutation, a NOTCH1 mutation, a SF3B1 mutation, a 11q deletion, or any combination thereof, comprising identifying a human in need of treatment for the lymphoma and having one of said deletions or mutations, and administering to said human a therapeutically effective amount of a compound of formula I:

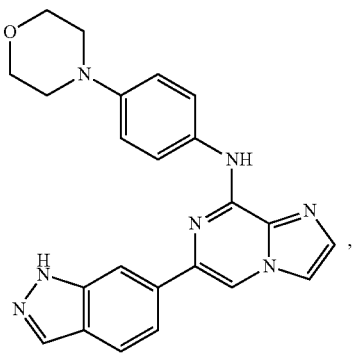

or a pharmaceutically acceptable salt thereof, wherein the compound of formula I or the pharmaceutically acceptable salt thereof is the only anti-cancer therapy administered to the human.

10. The method of claim 9, wherein the human has a 17p deletion, a TP53 mutation, or a combination thereof.

11. The method of claim 9, wherein the human has a NOTCH1 mutation, a SF3B1 mutation, a 11q deletion, or any combination thereof.

12. The method of claim 9, wherein the human is refractory to at least one anti-cancer treatment.

13. The method of claim 9, wherein the human is in relapse after treatment with at least one anti-cancer treatment.

14. The method of claim 9, wherein the lymphoma is non-Hodgkin's lymphoma.

15. A method for treating a B-cell lymphoma in a human having a 17p deletion, a TP53 mutation, a NOTCH1 mutation, a SF3B1 mutation, a 11q deletion, or any combination thereof, comprising identifying a human in need of treatment for the B-cell lymphoma and having one of said deletions or mutations, and administering to said human a therapeutically effective amount of a compound of formula I:

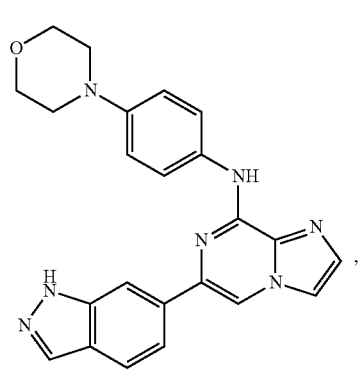

or a pharmaceutically acceptable salt thereof, wherein the compound of formula I or the pharmaceutically acceptable salt thereof is the only anti-cancer therapy administered to the human.

16. The method of claim 15, wherein the human has a 17p deletion, a TP53 mutation, or a combination thereof.

17. The method of claim 15, wherein the human has a NOTCH1 mutation, a SF3B1 mutation, a 11q deletion, or any combination thereof.

18. The method of claim 15, wherein the human is refractory to at least one anti-cancer treatment.

19. The method of claim 15, wherein the human is in relapse after treatment with at least one anti-cancer treatment.

* * * * *